US008173177B2

(12) United States Patent
Dao et al.

(10) Patent No.: US 8,173,177 B2
(45) Date of Patent: May 8, 2012

(54) COMPOSITIONS OF BOTANICAL EXTRACTS FOR CANCER THERAPY

(75) Inventors: James Dao, Henderson, NV (US); Tom C. S. Dao, Bellevue, WA (US); David D. Tong, Northridge, CA (US); Leslie Wilson, Carpinteria, CA (US); Mary Ann Jordan, Santa Barbara, CA (US); William Gerwick, Corvallis, OR (US)

(73) Assignee: Genyous Biomed International Inc., Henderson, NV (US)

( * ) Notice: Subject to any disclaimer, the term of this patent is extended or adjusted under 35 U.S.C. 154(b) by 219 days.

(21) Appl. No.: 10/937,707

(22) Filed: Sep. 8, 2004

(65) Prior Publication Data
US 2005/0208070 A1 Sep. 22, 2005

Related U.S. Application Data

(60) Provisional application No. 60/501,456, filed on Sep. 8, 2003.

(51) Int. Cl.
*A61K 36/00* (2006.01)
(52) U.S. Cl. ....................................................... 424/725
(58) Field of Classification Search ........................ None
See application file for complete search history.

(56) References Cited

U.S. PATENT DOCUMENTS

| | | | |
|---|---|---|---|
| 5,145,839 A | 9/1992 | Beljanski | |
| 5,437,866 A | 8/1995 | Sun | |
| 5,665,361 A | 9/1997 | Jann et al. | |
| 5,665,393 A * | 9/1997 | Chen et al. | 424/489 |
| 5,910,308 A | 6/1999 | D'Jang | |
| 5,952,471 A | 9/1999 | Griffiths Lawson | |
| 5,989,557 A | 11/1999 | Bombardelli et al. | |
| 6,168,795 B1 | 1/2001 | DJang | |
| 6,280,777 B1 | 8/2001 | Bombardelli et al. | |
| 6,299,925 B1 | 10/2001 | Xiong et al. | |
| 6,316,002 B1 | 11/2001 | Liu et al. | |
| 6,399,116 B1 | 6/2002 | Xiu | |
| 6,576,269 B1 | 6/2003 | Korneyev | |
| 2002/0177583 A1 | 11/2002 | Kiss | |
| 2005/0196409 A1 | 9/2005 | Dao et al. | |
| 2005/0214394 A1 | 9/2005 | Dao et al. | |

FOREIGN PATENT DOCUMENTS

| | | |
|---|---|---|
| CN | 1079361 A * | 12/1993 |
| CN | 1097621 A * | 1/1995 |
| CN | 1 105 588 A | 7/1995 |
| CN | 1104535 A * | 7/1995 |
| CN | 1120953 A * | 4/1996 |
| CN | 1 207 920 A | 2/1999 |
| CN | 1 232 690 A | 10/1999 |
| CN | 1 248 461 A | 3/2000 |
| CN | 1 273 119 A | 11/2000 |
| CN | 1 283 490 A | 2/2001 |
| CN | 1 305 754 A | 8/2001 |
| CN | 1 312 116 A | 9/2001 |
| CN | 1350865 A * | 5/2002 |
| CN | 1 480 209 A | 3/2004 |
| DE | 44 31 393 C1 | 2/1996 |
| EP | 0 938 897 A1 | 9/1999 |
| JP | 60-56924 A | 4/1985 |
| JP | 60-190719 A | 9/1985 |
| JP | 5-260903 A | 10/1993 |
| JP | 05328947 A * | 12/1993 |
| JP | 9-208484 A | 8/1997 |
| JP | 11-246402 A | 9/1999 |
| JP | 2001-163792 A | 6/2001 |
| JP | 2003183176 A * | 3/2003 |
| JP | 2004-217545 A | 8/2004 |
| JP | 2005-008539 A | 1/2005 |
| KR | 2001-074416 A | 8/2001 |
| KR | 2001-083663 A | 9/2001 |
| KR | 2002017675 A * | 3/2002 |
| KR | 2002-078314 A | 10/2002 |
| RU | 2 106 859 C1 | 3/1998 |
| RU | 2 120 272 C1 | 10/1998 |
| RU | 2 123 320 C1 | 12/1998 |
| RU | 2 129 003 C1 | 4/1999 |
| RU | 2 129 423 C1 | 4/1999 |
| RU | 2 132 183 C1 | 6/1999 |
| RU | 2 134 570 C1 | 8/1999 |
| RU | 2 158 599 C2 | 11/2000 |
| RU | 2 170 101 C1 | 7/2001 |
| RU | 2 183 964 C2 | 6/2002 |
| RU | 2 185 070 C2 | 7/2002 |
| WO | WO-02/22147 A1 | 3/2002 |
| WO | WO 02078722 A1 * | 10/2002 |
| WO | WO-2005/029963 A1 | 4/2005 |
| WO | WO-2005/044182 A2 | 5/2005 |
| WO | WO-2005/044182 A3 | 5/2005 |

OTHER PUBLICATIONS

Wong, B.Y., Mau B.H., Jia T.Y. and Wan C.P. 'Oldenlandia diffusa and Scutellaria barbata augment macrophage oxidative burst and inhibit tumor growth' Cancer Biother Radiopharm. vol. 11, No. 1 (Feb. 1996), pp. 51-56, PubMed Abstract.*
Kelly K. 'New Chemotherapy Agents for Small Cell Lung Cancer'. Chest, vol. 117, No. 4 (2000), pp. 156S-162S.*
Bunn P.A. and Kelly K. 'Combinations of three chemotherapeutic agents and two chemotherapeutic agents plus a targeted biologic agent in the treatment of advanced non small-cell lung cancer'. Clin Lung Cancer, vol. 2, No. Suppl. 1 (2000), pp. S23-S28. PubMed Abstract.*
Payne et al. (U1, Mayo Clinic Proceedings, 1997, 72(8):697-704).*
Kamb (Nature Reviews: Drug Discovery (2005), vol. 4, pp. 161-165).*

(Continued)

*Primary Examiner* — Amy L Clark
(74) *Attorney, Agent, or Firm* — Morrison & Foerster LLP

(57) ABSTRACT

Methods and compositions for prevention and therapy of cancer are provided. Compositions comprising therapeutically effective amounts of two or more of an extract of *Ganoderma lucidum*, an extract of *Salvia miltiorrhiza* and an extract of *Scutellaria barbata* and optionally a therapeutically effective amount of an extract of *Hippophae rhamnoides* are provided. Novel synergistic effects of the use of these compounds in combination therapy are disclosed. Embodiments further comprising therapeutically effective amounts of at least one chemotherapeutic agent are also provided.

14 Claims, 26 Drawing Sheets

OTHER PUBLICATIONS

Ames, B. N. et al. (Mar. 1973). "An Improved Bacterial Test System for the Detection and Classification of Mutagens and Carcinogens," *Proc. Natl. Acad. Sci. USA* 70(3):782-786.

Bai, Y.R. et al. (1994). "Hemodynamic Study on Nitroglycerin Compared with *Salvia miltiorrhiza*," Zhongguo Zhong Xi Yi Jie He Za Zhi (Chin. J. Intergr. Med.)14(1):4, 24-25. (Abstract on p. 4 in English only.).

Bensky, D. et al. eds. (1987). "Herbs That Stabilize and Bind" Chapter 13 In *A Chinese Botantical Medicine Materia Medica* Eastland Press: Seattle, WA pp. 375-394.

Briesewitz, R. et al. (Mar. 2, 1999). "Affinity Modulation of Small-Molecule Ligands by Borrowing Endogenous Protein Surfaces," *Proc. Natl. Acad. Sci. USA* 96(5): 1953-1958.

Brinkley, B.R. et al. (1998). "Supernumerary Centrosomes and Cancer: Boverie's Hypothesis Resurrected," *Cell Motility and the Cytoskeleton* 41(4):281-288.

Carroll, P.E. et al. (Mar. 18, 1999). "Centrosome Hyperamplification in Human Cancer: Chromosome Instability Induced by p53 Mutation and/or Mdm2 Overexpression," *Oncogene* 18(11):1935-1944.

Chan, G. et al. (Mar. 1, 1999). "Cyclooxygenase-2 Expression is Up-Regulated in Squamous Cell Carcinoma of the Head and Neck," *Cancer Res*. 59(5):991-994.

Chang, R. (1994). "Effective Dose of *Ganoderma* in Humans," *Proceedings of Contributed Symposium 59A,B, 5th International Mycological Congress*: Vancouver, Canada (Aug. 14-21, 1994), pp. 117-121.

Chen, Y. et al. (1990). "Chemical Composition and Characteristics of Seabuckthorn Fruit and its Oil," *Chem. Ind. Forest Prod*. 10(3):163-175. (Chinese Article, English Abstract).

Chou, T-C. (1991). "The Median-Effect Principle and the Combination Index for Quantitation of Synergism and Antagonism," Chapter 2 In *Synergism and Antagonism in Chemotherapy* Chou, T.C. et al. eds. Academic Press, Inc.: San Diego, CA pp. 61-102.

Chou, T-C. et al. (1984). "Quantitative Analysis of Dose-Effect Relationships: The Combined Effects of Multiple Drugs or Enzyme Inhibitors," *Adv. Enzyme Regul*. 22:27-55.

Compton, D.A. (Oct. 29, 1999). "New Tools for the Antimitotic Toolbox," *Science* 286:913-914.

Denkert, C. et al. (Jan. 1, 2001). "Expression of Cyclooxygenase 2 in Human Malignant Melanoma," *Cancer Res*. 61(1):303-308.

Donehower, R.C. et al. (1993). "Anticancer Drugs Derived From Plants," Section 9 In *Cancer: Principles and Practice of Oncology* Fourth Edition, J.B. Lippincott: Philadelphia, PA 1:409-417.

Doxsey, S. (Oct. 1998). "The Centrosome—A Tiny Organelle With Big Potential," *Nat. Genet*. 20(2): 104-106.

Forastiere, A.A. (Aug. 1993). "Use of Paclitaxel (TAXOL®) in Squamous Cell Carcinoma of the Head and Neck," *Semin. Oncol*. 20(4/Supp.3):56-60.

Geetha, S. et al. (Mar. 2002). "Anti-Oxidant and Immunomodulatory Properties of Seabuckthorn (*Hippophae rhamnoides*)—an in Vitro Study," *J. Ethnopharmacol*. 79(3):373-378.

Gennaro, A. ed. (1990). *Remington's Pharmaceutical Science*, 18th Edition, Lippincott Williams & Wilkins pp. xv-xvi. (Table of Contents Only.).

Goel, H.C. et al. (Jan. 2002). "Radioprotection by a Herbal Preparation of *Hippophae rhamnoides*, RH-3, Against Whole Body Lethal Irradiation in Mice," *Phytomedicine* 9(1):15-25.

Hinchcliffe, E.H. et al. (Feb. 5, 1999). "Requirement of Cdk2-Cyclin E Activity for Repeated Centrosome Reproduction in *Xenopus* Egg Extracts," *Science* 283:851-854.

International Search Report mailed Jun. 8, 2005, for PCT Application No. PCT/US04/29263 filed Sep. 8, 2004, 6 pages.

Jankun, J. et al. (Jun. 5, 1997). "Why Drinking Green Tea Could Prevent Cancer," *Nature* 387:561.

Jordan, M.A. et al. (Apr. 2004). "Microtubules as a Target for Anticancer Drugs," *Nature Reviews Cancer* 4:253-265.

Kelley, D.S. (May/Jun. 1992). "Alpha-Linolenic Acid and Immune Response," *Nutrition* 8(3):215-217.

Kingston, D.G.I. (Jun. 1994). "Taxol: The Chemistry and Structure-Activity Relationships of a Novel Anticancer Agent," *Trends Biotechnol*. 12:222-227.

Kuo, K-K. et al. (Jan. 2000). "Centrosome Abnormalities in Human Carcinomas of the Gallbladder and Intrahepatic and Extrahepatic Bile Ducts," *Hepatology* 31(1):59-64.

Lingle, W.L. et al. (Mar. 17, 1998). "Centrosome Hypertrophy in Human Breast Tumors: Implications for Genomic Stability and Cell Polarity," *Proc. Natl. Acad. Sci. USA* 95(6):2950-2955.

Llovera, M. et al. (Jul. 25, 1998). "Role of TNF Receptor 1 in Protein Turnover During Cancer Cachexia Using Gene Knockout Mice," *Mol. Cell Endocrinol*. 142(1-2): 183-189.

McGuire, W.P. et al. (Aug. 15, 1989). "Taxol: A Unique Antineoplastic Agent with Significant Activity in Advanced Ovarian Epithelial Neoplasms," *Ann. Int. Med*. 111(4):273-279.

Nagai, M. et al. (Feb. 1996). "Vasodilator Effects of Des(Alpha-carboxy-3,4-dihydroxyphenethyl)lithospermic Acid (8-Epibtechnic Acid), a Derivative of Lithospermic Acids in *Salviae miltiorrhizae* Radix," *Biol. Pharm. Bull*. 19(2):228-232.

Nairn, J.G. (2000). "Solution, Emulsions, Suspensions, and Extracts" Chapter 39 In *Remington's Pharmaceutical Science*, 20th Edition Lippincott Williams & Wilkins, pp. 721-752.

Ngan, V.K. et al. (Jul. 2001). "Mechanism of Mitotic Block and Inhibition of Cell Proliferation by the Semisynthetic *Vinca* Alkaloids Vinorelbine and its Newer Derivative Vinflunine," *Mol. Pharmacol*. 60(1):225-232.

Paintrand, M. et al. (Mar./Apr. 1992). "Centrosome Organization and Centriole Architecture: Their Sensitivity to Divalent Cations," *J. Struct. Biol*. 108(2):107-128.

Pihan, G.A. et al. (Sep. 1, 1998). "Centrosome Defects and Genetic Instability in Malignant Tumors," *Cancer Res*. 58:3974-3985.

Raloff, J. (Apr. 11, 1998). "Drug Prevents Some Cancer, Poses Risks," *Science News* 153(15):228.

Rowinsky, E.K. et al. (Aug. 1, 1990). "Taxol: A Novel Investigational Antimicrotubule Agent," *J. Nat. Cancer Inst*. 82(15):1247-1259.

Sato, N. et al. (May 1999). "Centrosome Abnormalities in Pancreatic Ductal Carcinoma," *Clin. Cancer. Res*. 5(5):963-970.

Schiff, P.B. et al. (Feb. 22, 1979). "Promotion of Microtubule Assemby in vitro by Taxol," *Nature* 277:665-667.

Skehan, P. et al. (Jul. 4, 1990). "New Colorimetric Cytotoxicity Assay for Anticancer-Drug Screening," *J. Natl. Cancer. Inst*. 82(13):1107-1112.

Smith, T.J. et al. (Sep. 15, 1993). "Efficacy and Cost-Effectiveness of Cancer Treatment: Rational Allocation of Resources Based on Decision Analysis," *J. Natl. Cancer. Inst*. 85(18):1460-1474.

Süleyman, H. et al. (Nov. 2001). "Antiulcerogenic Effect of *Hippophae rhamnoides* L.," *Phytother. Res*. 15(7):625-627.

Svensson, H. et al. (May-Jun. 1995). "Quality Assurance in Radiotherapy," *World Health* 48(3):22-23.

Tucker, O.N. et al. (Mar. 1, 1999). "Cyclooxygenase-2 Expression is Up-Regulated in Human Pancreatic Cancer," *Cancer Res*. 59(5):987-990.

Vane, J.R. et al. (Mar. 1994). "Inducible Isoforms of Cyclooxygenase and Nitric-Oxide Synthase in Inflammation," *Proc. Natl. Acad. Sci. USA* 91(6):2046-2050.

Weber, R.G. et al. (1998). "Centrosome Amplification as a Possible Mechanism for Numerical Chromosome Aberrations in Cerebral Primitive Neuroectodermal Tumors with TP53 Mutations," *Cytogenet. Cell. Genet*. 83:266-269.

Wilson, L. et al. (1999). "Modulation of Microtubule Dynamics by Drugs: A Paradigm for the Actions of Cellular Regulators," *Cell Struct. & Function* 24:329-335.

Wong, B.Y.Y. et al. (1993). "Inhibition of Dexamethasone-Induced Cytochrome P450-Mediated Mutagenicity and Metabolism of Aflatoxin $B_1$ by Chinese Medicinal Herbs," *Eur. J. Cancer Prev*. 2:351-356.

Wong, B.Y.Y. et al. (Feb. 1996). "*Oldenlandia diffuse* and *Scutellaria barbata* Augment Macrophage Oxidative Burst and Inhibit Tumor Growth," *Cancer Biother. Radiopharm*. 11(1):51-56.

Wong, B.Y.Y. et al. (Jun. 1, 1992). "Chinese Medicinal Herbs Modulate Mutagenesis, DNA Binding and Metabolism of Aflatoxin $B_1$," *Mutat. Res*. 279(3):209-216.

Wu, Y-J. et al. (1998). "Increase of Vitamin E Content in LDL and Reduction of Atherosclerosis in Cholesterol-Fed Rabbits by a Water-Soluble Antioxidant-Rich Fraction of *Salvia miltiorrhiza*," *Arterioscler. Thromb. Vasc. Biol*. 18:481-486.

Xu, X. et al. (Mar. 1999). "Centrosome Amplification and a Defective $G_2$-M Cell Cycle Checkpoint Induce Genetic Instability in BRCA1 Exon 11 Isoform-Deficient Cells," *Mol. Cell* 3(3):389-395.

Yang, B. et al. (Jun. 2000). "Effect of Dietary Supplementation with Sea Buckthorn (*Hippophaë thamnoides*) Seed and Pulp Oils on the Fatty Acid Composition of Skin Glycerophospholipids of Patients with Atopic Dermatitis," *J. Nutr. Biochem*. 11(6):338-340.

Zhang, W. et al. (2003). "Determination of Scutellarin in *Scutellaria barbata* Extract by Liquid Chromatography-Electrochemical Detection," *Journal of Liquid Chromatography & Related Technologies* 26(13):2133-2140.

Anonymous. (Apr. 2003). "Plants for a Future: Database Search Results: *Scutellaria barbata*," located at <http://web.archive.org/web/20030403070746/http://www.ibiblio.org/pfaf/cgi-bin/arr_.html> last visited Feb. 28, 2006, two pages.

Li, T. et al. (1991). "Prevention of Tumour Production in Rats Fed Aminopyrine Plus Nitrite by Sea Buckthorn Juice," *IARC Sci. Publ.* 105:568-570.

Yun, T-K. (1999). "Update from Asia: Asian Studies on Cancer Chemoprevention," *Ann. NY Acad. Sci.* 889:157-192.

Dermer, G.B. (Mar. 1994). "Another Anniversary for the War on Cancer," *Bio/Technology* 12:320.

Freshney, R.I. (1983). *Culture of Animal Cells: A Manual of Basic Technique*, Alan R. Liss, Inc.: New York, NY, p. 4 and pp. vii-xii (Table of Contents.).

Tao, X. et al. (Jan. 1998). "Effects of *Tripterygium wilfordii* Hook F Extracts on Induction of Cyclooxygenase 2 Activity and Prostaglandin $E_2$ Production," *Arthritis & Rheumatism* 41(1):130-138.

Anonymous. (1986). Definition of *Scutelleria barbata*, *Dictionary of Chinese Herbal Medicines*, edited by New Medical College of Jiangsu, First Edition, Shanghai Science & Technology Press, three pp. (English Translation.).

Beveridge, T. et al. (Jan. 2, 2002, e-pub. Nov. 22, 2001). "Processing Effects on the Composition of Sea Buckthorn Juice from *Hippophae rhamnoides* L. Cv. Indian Summer," *J. Agri. Food Chem.* 50(1):113-116.

Bourgeois, C. (1992). *Determination of Vitamin E: Tocopherols and Tocotrienols*, Elsevier Applied Science, Essex, England pp. v-vi. (Table of Contents Only.).

Cheng, J. et al. (2003). "Inhibitory Effects of Total Flavones of *Hippophae rhamnoides* L on Thrombosis in Mouse Femoral Artery and in vitro Platelet Aggregation," *Life Sciences* 72:2263-2271.

Chou, T-C. et al. (Nov. 1983). "Analysis of Combined Drug Effects: A New Look at a Very Old Problem," *Trends Pharmacol. Sci.* 4(11):450-454.

Eccleston, C. et al. (Jun. 2002). "Effects of an Antioxidant-Rich Juice (Sea Buckthorn) on Risk Factors for Coronary Heart Disease in Humans," *J. Nutr. Biochem.* 13(6):346-354.

Gao, Z-L. et al. (Jul. 15, 2003). "Effect of Sea Buckthorn on Liver Fibrosis: A Clinical Study," *World J. Gastroentrol.* 9(7):1615-1617.

Geetha, S. et al. (Nov. 2002). "Effect of Seabuckthorn on Sodium Nitroprusside-Induced Cytotoxicity in Murine Macrophages," *Biomed. Pharmacother.* 56(9):463-467.

Goel, H.C. et al. (Mar. 2003). "Induction of DNA-Protein Cross-Links by *Hippophae rhamnoides*: Implications in Radioprotection and Cytotoxicity," *Molecular and Cellular Biochemistry* 245(1/2):57-67.

Goel, H.C. et al. (Mar. 2003). "Protection of Jejunal Crypts by RH-3 (A Preparation of *Hippophae rhamnoides*) Against Lethal Whole Body Gamma Irradiation," *Phytother. Res.* 17(3):222-226.

Goel, H.C. et al. (2004). "Induction of Apoptosis in Thymocytes by *Hippophae rhamnoides*: Implications in Radioprotection," *Journal of Environmental Pathology, Toxicology, and Oncology* 23(2):123-137.

Gokmen, V. et al. (1996). "A Simple HPLC Method for the Determination of Total Vitamin C in Fruit Juices and Drinks," *Fruit Processing* 5:198-201.

International Search Report mailed on Jan. 31, 2005, for PCT Application No. PCT/US04/31986 filed on Sep. 22, 2004, three pages.

Li, T.S.C. et al. (Oct./Dec. 1996). "Sea Buckthorn (*Hippophae rhamnoides* L.): A Multipurpose Plant," *Hort. Tech.* 6(4):370-380.

Nersessian, A.K. (1990). "The Antimutagenic Action of Sea-Buckthorn Oil," *Genetika* 26(2):378-380. (Article in Russian, Abstract in English).

Nikulin, A.A. et al. (1992). "Comparative Pharmacological Estimation of *Hippophae*, Rosa and Plantain Oils in Experimental Eye Burns," *Eksp. Klin. Farmakol.* 55(4):64-66. (Article in Russian, Abstract in English).

Pellegrini, N. et al. (1999). "Screening of Dietary Carotenoids and Carotenoid-Rich Fruit Extracts for Antioxidant Activities Applying 2,2'-Azinobis(3-ethylenebenzothiazoline-6-sulfonic Acid Radical Cation Decolorization Assay," Chapter 34 in *Methods in Enzymology*, Packer, L. ed., Academic Press, Inc. 299:379-389.

Rösch, D. et al. (Jul. 16, 2003, e-pub. Jun. 20, 2003). "Structure-Antioxidant Efficiency Relationships of Phenolic Compounds and Their Contribution to the Antioxidant Activity of Sea Buckthorn Juice," *J. Agri. Food Chem.* 51(15):4233-4239.

Süleyman, H. et al. (Sep. 2002). "Beneficial Effects of *Hippophae rhamnoides* L. on Nicotine Induced Oxidative Stress in Rat Blood Compared with Vitamin E," *Biol. Pharm. Bull.* 25(9):1133-1136.

Supplementary European Search Report mailed Sep. 24, 2007, for EP Application No. 04 78 9256.7, filed Sep. 22, 2004, four pages.

Velioglu, Y.S. et al. (Oct. 1998, e-pub. Aug. 29, 1998). "Antioxidant Activity and Total Phenolics in Selected Fruits, Vegetables, and Grain Products," *J. Agri. Food Chem.* 46(10):4113-4117.

Vinson, J.A. et al. (Sep. 1998, e-pub. Aug. 22, 1998). "Phenol Antioxidant Quantity and Quality in Foods: Vegetables," *J. Agri. Food Chem.* 46(9):3630-3634.

Anonymous. (Date Unknown). "*Scutellaria barbata*," Memorial Sloan-Kettering Cancer Center, downloaded from <http://www.mskcc.org/tmskcc/print/69367.cfm>, last visited on Oct. 12, 2010, 3 pages.

Anonymous. (Jan. 16, 2004). "Reports of Tanshinones Found in the Literature," 2 pages.

Anonymous. (Nov. 10, 2003). "Royal Tongan Limu Dietary Supplements Promoted to Treat Various Diseases Destroyed," *FDA News* 1 page.

Cohen, I. et al. (Dec. 2002). "Traditional Chinese Medicine in the Treatment of Breast Cancer," *Seminars in Oncology* 29(6):563-574.

Cohen, I. et al. (Feb. 2002). "(Part One) Traditional Chinese Medicine in the Treatment of Breast Cancer," *Journal of Chinese Medicine* 68:40-49.

Dharmananda, S. (Date Unknown). "Oldenlandia and Scutellaria Antitoxin and Anticancer Herbs," *ITM Online*, downloaded from <http://www.itmonline.org/arts/oldenlandia.htm>, last visited on Oct. 6, 2010, 8 pages.

Johnson, J.I. et al. (2001). "Relationships Between Drug Activity in NCI Preclinical in vitro and in vivo Models and Early Clinical Trials," *British Journal of Cancer* 84(10):1424-1431.

Meyer, J.P. et al. (2002). "PC-SPECTS: A Herbal Therapy for the Treatment of Hormone Refractory Prostate Cancer," *Prostate Cancer and Prostatic Diseases* 5(1):13-15.

SHJi, Q. (2000). "Shaji—Miracle Plant in Nature," *Macro Review* 13(1):51-57. (Chinese Language).

Sudbø, J. et al. (2003). "Cyclooxygenase-2 (COX-2) Expression in High-Risk Premalignant Oral Lesions," *Oral Oncology* 39:497-505.

Tan, B.K.H. et al. (2004). "Immunomodulatory and Antimicrobial Effects of Some Traditional Chinese Medicinal Herbs: A Review," *Current Medicinal Chemistry* 11(11):1423-1430.

Voskoglou-Nomikos, T. et al. (Sep. 15, 2003). "Clinical Predictive Value of the in vitro Cell Line, Human Xenograft, and Mouse Allograft Preclinical Cancer Models," *Clinical Cancer Research* 9:4227-4239.

Yuan, S.L. et al. (Dec. 2003). "Anticancer Effect of Tanshinone and its Mechanisms," *PubMed* 22(12):1363-1366. (Abstract Only).

Furusawa, E. et al. (1992). "Antitumour Activity of *Ganoderma lucidum*, an Edible Mushroom, on Intraperitoneally Implanted Lewis Lung Carcinoma in Synergenic Mice," *Phytotherapy Research* 6(6):300-304.

Hirose, S. (Mar. 1998). "A Case of Liver Cancer in Which a Tumor was Shrunk Through Traditional Chinese Herbal Therapy," *Lecture for 7th Meeting of Traditional Chinese Herbal Therapy*, Mar. 1998, 45(3):314-317. with English Translation, 10 pages total.

Lee, S-S. et al. (2003). "Antitumor Effects of Polysaccharides of *Ganoderma lucidum* (Curt.:Fr.) P. Karst. (Ling Zhi, Reishi mushroom) (Aphyllophoromycetideae)," *International Journal of Medicinal Mushrooms* 5(1):1-16.

Lee, C-H. et al. (2005). "Successful Establishment in Scid Mice of Human Ovarian Tumor Tissue Xenografts Derived from a Broad Spectrum of Primary Tumors," 1 page.

Shii, Q. (2000). "Shaji—Miracle Plant in Nature," *Macro Review* 13(1):51-57. (Chinese Language).

Wang, Y. et al. (2003). "A Novel Prostate Cancer Tissue Xenograft Metastasis Model," 1 page.

\* cited by examiner

Note: E = Estramustine Sodium Phosphate
D = Docetaxel

COMPOSITIONS OF BOTANICAL EXTRACTS FOR CANCER THERAPY

CROSS-REFERENCE TO RELATED APPLICATIONS

This application claims the benefit of priority to U.S. Provisional Application No. 60/501,456, filed Sep. 8, 2003 the contents of which is incorporated by reference herein in its entirety.

TECHNICAL FIELD OF THE INVENTION

This invention relates generally to the field of using botanical extracts for ameliorating disease states. More specifically, the invention provides methods and compositions of botanical extracts for use in prevention and therapy of disease states including cancer.

BACKGROUND OF THE INVENTION

Any one individual is at risk of developing cancer. The occurrence of cancer increases with aging over a life time ("lifetime risk"). For example, in the U.S., men have a 1 in 2 lifetime risk of developing cancer, and women have a 1 in 3 risk. Other risk factors are believed to include genetics, diet, and environmental exposure (e.g., to mutagenic chemicals, radiation, transforming viruses, etc.). It is estimated by the World Health Organization that about 10 million new cancer cases are occurring now annually around the world. That number is expected to reach 15 million by the year 2015, with two thirds of these new cases occurring in developing countries (World Health 48:22, 1995). For example, it is estimated that there is about 600,000 new cases of lung cancer per year worldwide; approaching 1 million new cases of breast cancer per year; and for head and neck cancer (the sixth most frequently occurring cancer worldwide) an incidence of 500,000 new cases annually. The National Cancer Institute of the United States estimates the overall annual costs for cancer at $107 billion. Treatment costs account for approximately $40 billion.

Several chemotherapeutic agents are in use in the treatment of cancer, including alkylating agents, antimetabolites antagonists, anticancer antibiotics, and plant-derived anticancer agents. Examples of "alkylating agents" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, carboquone, adozelesin, cystemustine, and bizelesin. Examples of "antimetabolites" include mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emmitefur), aminopterine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, and ambamustine, etc. Examples of "anticancer antibiotics" include actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, and idarubicin hydrochloride, etc. Examples of "plant-derived anticancer agents" include etoposide phosphate, vinblastine sulfate, vincristine sulfate, vindesine sulfate, teniposide, paclitaxel, docetaxel, and vinorelbine, etc.

While new therapeutics are being developed and tested for efficacy against tumors, many of the currently available cancer treatments are relatively ineffective. It has been reported that chemotherapy results in a durable response in only 4% of treated patients, and substantially prolongs the life of only an additional 3% of patients with advanced cancer (Smith et al., 1993, J. Natl. Cancer Inst. 85:1460-1474). Many of the current anticancer drugs are both cost-prohibitive, and present with major toxicity. Regarding the latter and depending on the drug or drug combination used, systemic chemotherapy may result in one or more toxicities including hematologic, vascular, neural, gastrointestinal, renal, pulmonary, otologic, and lethal. For example, tamoxifen has been used in women for 25 years to limit breast cancer recurrence. A trial launched in 1992 has shown that tamoxifen is not only effective as a therapeutic agent, but also has a very substantial benefit in cancer prevention (a breast cancer preventative agent). However, in that study, tamoxifen use was shown to have adverse effects in healthy women; i.e., an increased risk of developing uterine cancer or pulmonary blood clots (Science News, 1998, 153:228).

Plants are a valuable resource for the discovery and development of novel, naturally derived agents to treat cancer. Drugs that are currently used in cancer therapy were designed to perturb microtubule shortening (depolymerization) or lengthening (polymerization) (Compton, D. A., et al., (1999) Science 286:913-914). The centrosome, the major microtubule organizing center (MTOC) of the cell, is composed of two centrioles surrounded by the so-called pericentriolar material (PCM), which consists of a complex thin filament network and two sets of appendages (Paintrand, M. (1992) J Struct Biol 108:107-128). The main function of the centrosome is the nucleation of microtubules and the formation of bipolar spindles (Tanaka, T., et al., (1999) Cancer Res 58(17): 3974-85). Centrosomes and their associated microtubules direct events during mitosis and control the organization of animal cell structures and movement during interphase. Malignant tumors generally display abnormal centrosome profiles, characterized by an increase in size and number of centrosomes, by their irregular distribution, abnormal structure, aberrant protein phosphorylation, and by increased microtubule nucleating capacity in comparison to centrosomes of normal tissues (Lingle, W. L. et al., (1998) Proc Natl Acad Sci USA 95(6): 2950-5; Sato. N., et al., (1999) Clin Cancer Res 5(5):963-70; Pihan, G. A. et al., (1998) Cancer Res 58(17):3974-85; Carroll, P. E., et al., (1999) Oncogene 18(11): 1935-44; Xu, X., et al., (1999) Mol Cell 3(3):389-95; Brinkley, B. R., et al., (1998) Cell Motil Cytoskeleton 41(4):281-8; Doxsey, S. (1998) Nat Genet 20(2):104-6; Kuo, K. K., et al., (2000) Hepatology 31(1):59-64). Among the abnormalities, centrosome hyperamplification is found to be more frequent in a variety of tumor types (Carroll, P. E., et al., (1999) Oncogene 18; 18(11):1935-44; Hinchcliffe, E. H., et al., (1999) Science 283(5403):851-4; Xu, X., et al., (1999) Mol Cell 3(3):389-95; Weber, R. G., et al., (1998) Cytogenet Cell Genet 83:266-269).

A variety of drugs, such as paclitaxel, docetaxel, etoposide, vincristine, vinblastine, and vinorelbine, currently used in cancer therapy were designed to perturb microtubule polymerization (for review, see Jordan M A and Wilson L., *Microtubules as a target for anticancer drugs*. Nature Reviews Cancer 4:253-265 (2004)). They share a common mechanism of action of binding to tubulin, the molecule of which microtubules are composed. (Compton, D. A., et al., (1999) Science 286:913-914; Wilson, L., et al. Cell Struct. & Function 24:329-335 (1999)). At least six plant-derived anticancer agents have received FDA approval (e.g., taxol, vinblastine, vincristine, topotecan, etoposide, teniposide). Other agents are being evaluated in clinical trials (e.g., camptothecin, 9AC, and irinotecan).

Taxol, a diterpenoid originally isolated from the bark of the Pacific yew, *Taxus brevifolia*, is a powerful antimitotic agent that acts by promoting tubulin assembly into stable aggregated structures. (see review Kingston, D. G. I. Trends Biotechnol. 1994, 12, 222; Schiff, P. B.; Fant, J.; Horwitz, S. B. Nature, 1979, 277, 665). Taxol has shown tremendous potential as an anticancer compound. Indeed, it is now used for the treatment of refractory ovarian cancer, and clinical trials are encouraging for the treatment of breast, lung, head, and neck cancers. (Rowinsky, E. K.; Cazenave, L. A.; Donehower, R. C. J. Nat. Cancer Inst. 1990, 82, 1247; McGuire, W. P.; Rowinsky, E. K.; Rosenshein, N. B.; Grumbine, F. C.; Ettinger, D. S.; Armstrong, D. K.; Donehower, R. C. Ann. Int. Med. 1989, 11, 273; Forastiere, A. A., Semin. Oncol. Suppl. 3. 1993, 20, 56).

Vinca alkaloids, including the natural products vincristine and vinblastine and the semisynthetic derivatives vindesine and vinorelbine, are antimitotic drugs that are widely used in cancer treatment (Donehower R C and Rowinsky E K, Anticancer drugs derived from plants, in *Cancer: Principles and Practice of Oncology*. De Vita V T, Hellman S and Rosenberg S A eds. pp 409-417, JB Lippincott, Philadelphia. (1993)). Second-generation Vinca alkaloids, vinorelbine and vinflunine, affect microtubule dynamics differently from vinblastine, a first generation Vinca alkaloid which strongly suppresses the rate and extent of microtubule shortening in vitro, whereas vinorelbine and vinflunine suppress the rate and extent of microtubule growing events (Ngan V. K. et al., Mol Pharmacol. 60(1):225-232 (2001)).

Chemopreventive agents being investigated for the ability of reducing the amount of pre-cancerous cells in the lungs of smokers and ex-smokers include ACAPHA, a combination of six botanicals (*Sophora tonkinensis, Polygonum bistorta, Prunella vulgaris, Sonchus brachyotus, Dictamnus dasycarpus* and *Dioscorea bulbifera*) which has been used for disease prevention in China for centuries. Under a US National Cancer Institute grant, the British Columbia Cancer Agency (Canada) is leading an international consortium in carrying out the phase II clinical trials of ACAPHA.

Cancer implicates several important signal pathways in the cell such as growth control pathways (20 percent of the known types of cancer, including some breast and brain cancers). The same pathways also play key roles in the autoimmune response signal pathway, so inhibitors of the pathway have potential use as immuno-suppressive and anti-inflammation drugs. Combining drug compounds with certain naturally occurring proteins have been shown as an alternative way to produce improved pharmaceuticals, particularly immuno-suppressive, anti-inflammation and anti-cancer drugs. (Briesewitz R, Ray G T, Wandless T J, Crabtree G R., Affinity modulation of small-molecule ligands by borrowing endogenous protein surfaces. Proc Natl Acad Sci USA. (1999) March 2; 96(5):1953-1958).

There is a need for a relatively cost-effective and efficient method for preventing tumors and inhibiting growth of tumors, which additionally ameliorates the toxicity generally associated with systemic chemotherapy. Anticancer compositions comprising *Gynostemma pentaphyllum* extract, *Camellia sinensis* (green tea) and *Crataegus pinnatifida* (hawthorn berries) and a method of making the same is the subject of U.S. Pat. Nos. 5,910,308 and 6,168,795 (DJang).

SUMMARY OF THE INVENTION

The present invention provides novel compositions, extracts and compounds comprising botanical extracts and their methods for manufacture and preparation. Use of such compounds in the prevention and therapy of disease states (including cancer) are also provided as are methods for preparation and formulation of the compositions as well as methods for treatment using the compositions of this invention.

The compositions comprise therapeutically effective amounts of two or more of an extract of *Ganoderma lucidum* (GL), an extract of *Salvia miltiorrhiza* (SM) and an extract of *Scutellaria barbata* (SB); and optionally a therapeutically effective amount of an extract of *Hippophae rhamnoides* (HR). Whereas there are reports of health benefiting effects of these individual botanicals, the synergistic effects of their use in combination therapy, as disclosed in this invention is novel. Some embodiments further comprise a therapeutically effective amount of at least one chemotherapeutic agent.

The present invention relates to compositions for use in cancer treatment and methods for their preparation, formulation, and administration in the prevention and therapy of disease states.

The compositions of the present invention comprise natural compounds that exhibit cytostatic effects for use in inhibiting further growth of pre-existing cancer cells by exhibiting one or more properties of (i) boosting the immune system, (ii) reducing oxidative damage to cells and tissues, (iii) reducing inflammation, (iv) arresting proliferation of cells in certain stages of the cell cycle, (v) anti-oxidant activity, and (vi) anti-mutagenic effects against further exposure to carcinogens and mutagens.

The compositions of the present invention comprise natural compounds that are useful in cytotoxic compositions to be administered in conjunction with chemotherapeutic agents, radiation treatment and surgery. In some embodiments, a subject is administered compositions of the present invention prior to radiation therapy, chemotherapy or surgery. In other embodiments, the compositions are administered simultaneously with other anti-cancer therapy. These compositions exhibit one or more properties of (a) synergistic action with chemotherapy (increasing sensitivity to chemotherapeutic agents), (b) synergistic action with radiation therapy and surgery (increasing effectiveness by inhibiting growth of pre-existing cancer cells that are missed by radiation or surgery) in addition to the previously stated properties of (i) boosting the immune system, (ii) reducing oxidative damage to cells and tissues, (iii) reducing inflammation, (iv) arresting proliferation of cells in certain stages of the cell cycle, (v) anti-oxidant activity, and (vi) anti-mutagenic effects against further exposure to carcinogens and mutagens. Anti-mutagenic properties (together with increased sensitivity by synergism) reduce levels of chemotherapeutic agents necessary for treatment thus resulting in reduced toxicity for patients. The compositions of the present invention are useful in conjunction with chemotherapeutic agents including alkylating agents, antimetabolites antagonists, anticancer antibiotics, and plant-derived anticancer agents.

Examples of "alkylating agents" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, carboquone, adozelesin, cystemustine, and bizelesin.

Examples of "antimetabolites" include mercaptopurine, 6-mercaptopurine riboside, thioinosine, methotrexate, enocitabine, cytarabine, cytarabine ocfosfate, ancitabine hydrochloride, 5-FU (5-fluorouracil) drugs (e.g., fluorouracil, tegafur, uracil/ftorafur (UFT®), doxifluridine, carmofur, gallocitabine, emmitefur), aminopterine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, and ambamustine, etc.

Examples of "anticancer antibiotics" include actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, and idarubicin hydrochloride, etc.

Examples of "plant-derived anticancer agents" include etoposide phosphate, vinblastine sulfate, vincristine sulfate, vindesine sulfate, teniposide, paclitaxel, docetaxel, and vinorelbine, etc.

The cytotoxic compositions of the present invention may also be used in conjunction with immunotherapeutic agents including picibanil, krestin, sizofiran, lentinan, ubenimex, interferons, interleukins, macrophage colony-stimulating factor, granulocyte colony-stimulating factor, erythropoietin, lymphotoxin, BCG vaccine, *Corynebacterium parvum*, levamisole, polysaccharide K, and procodazole.

While some compounds of the present invention have been known to demonstrate health benefits when administered individually, the present invention relates to novel combinations of natural compounds that demonstrate the properties of the compositions when administered as specified combinations. In general, the specific compositions of the present invention exhibit synergistic enhancement of their efficacies when administered in combination.

The present invention and other objects, features, and advantages of the present invention will become further apparent in the following Detailed Description of the Invention and the accompanying Figures and embodiments.

DETAILED DESCRIPTION OF THE INVENTION

Figure 1A:
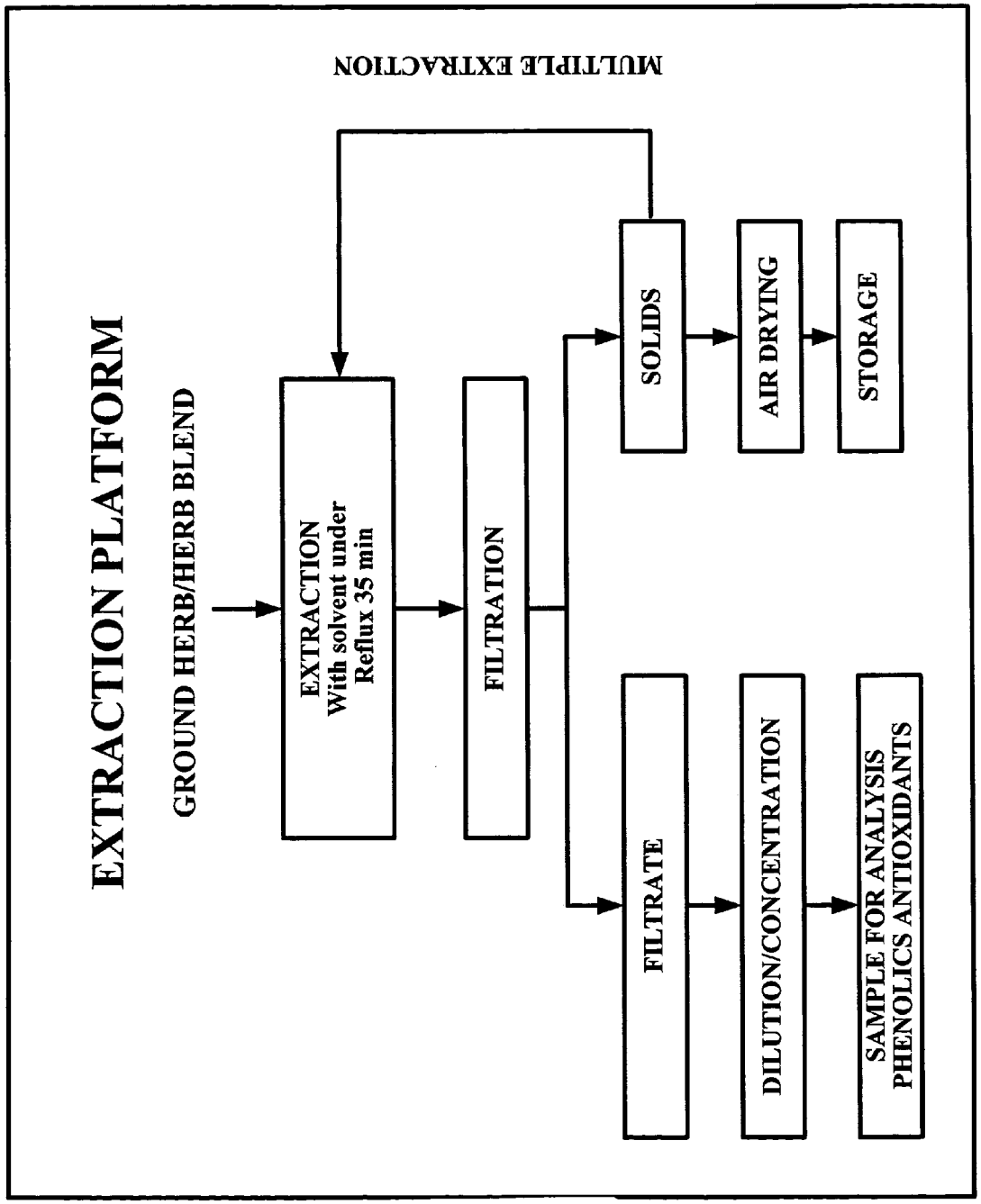
FIG. 1 shows an extraction platform for botanical extracts.
Figure 1B:
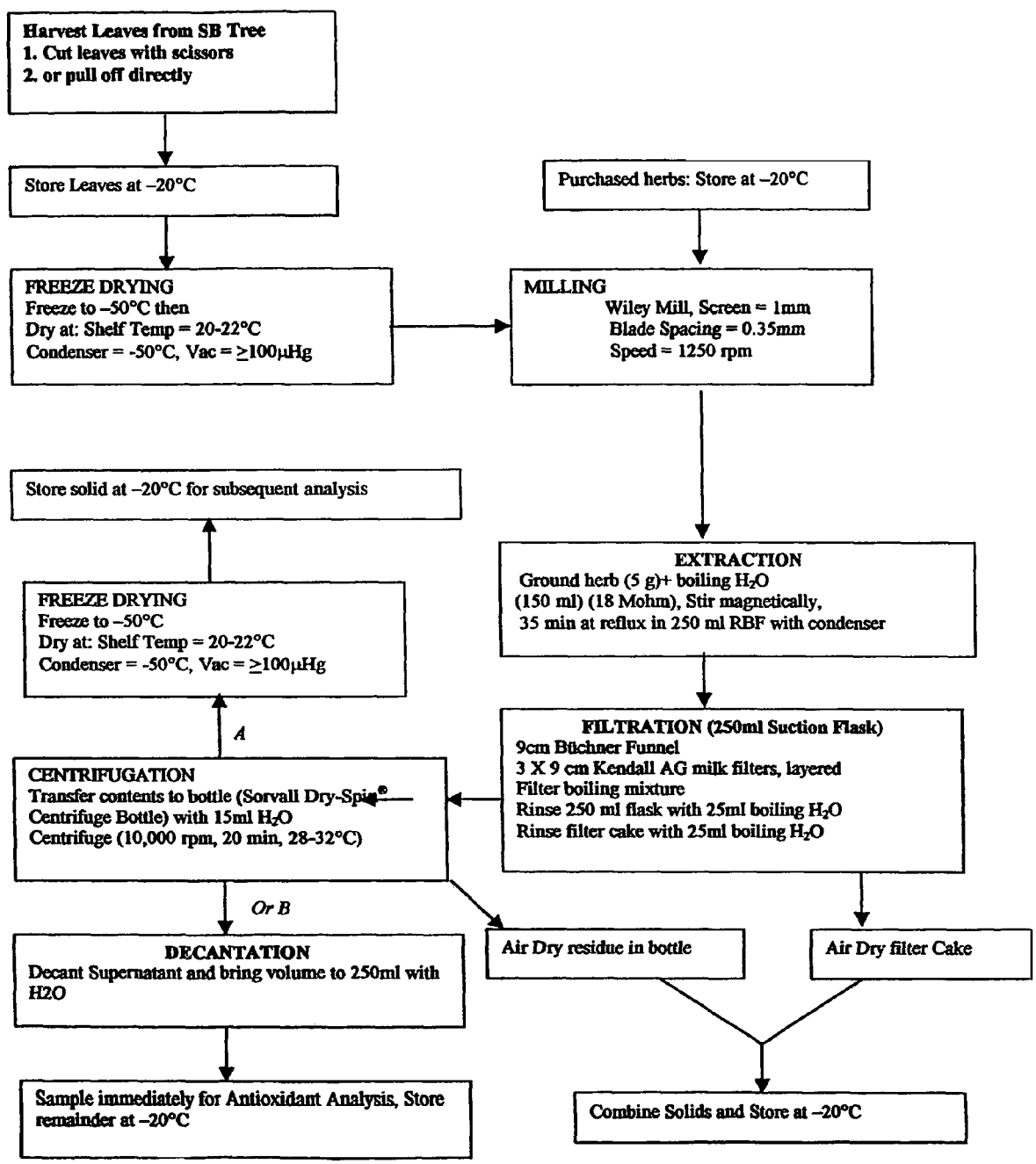
Figure 1C:
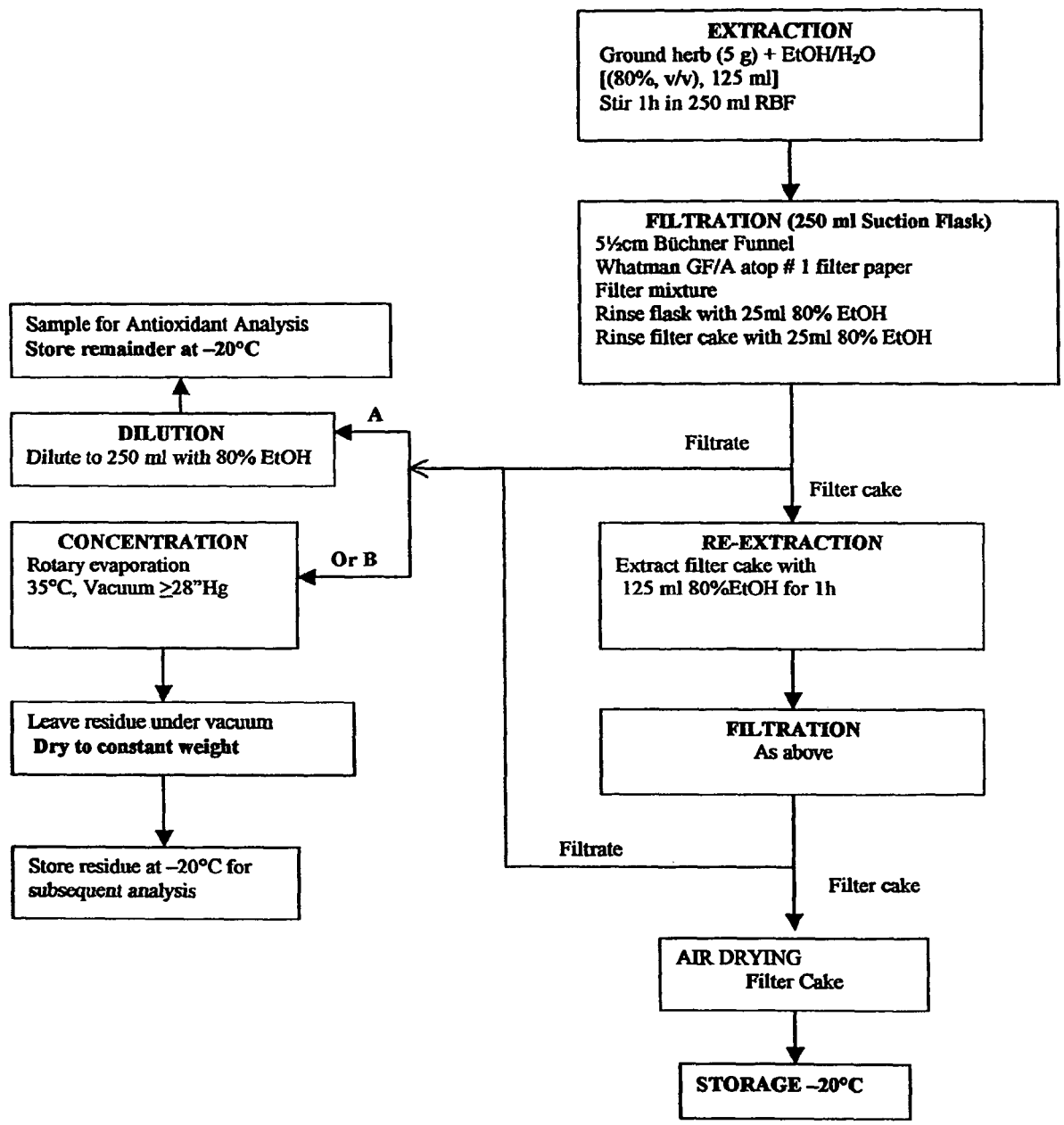
Figure 1D:
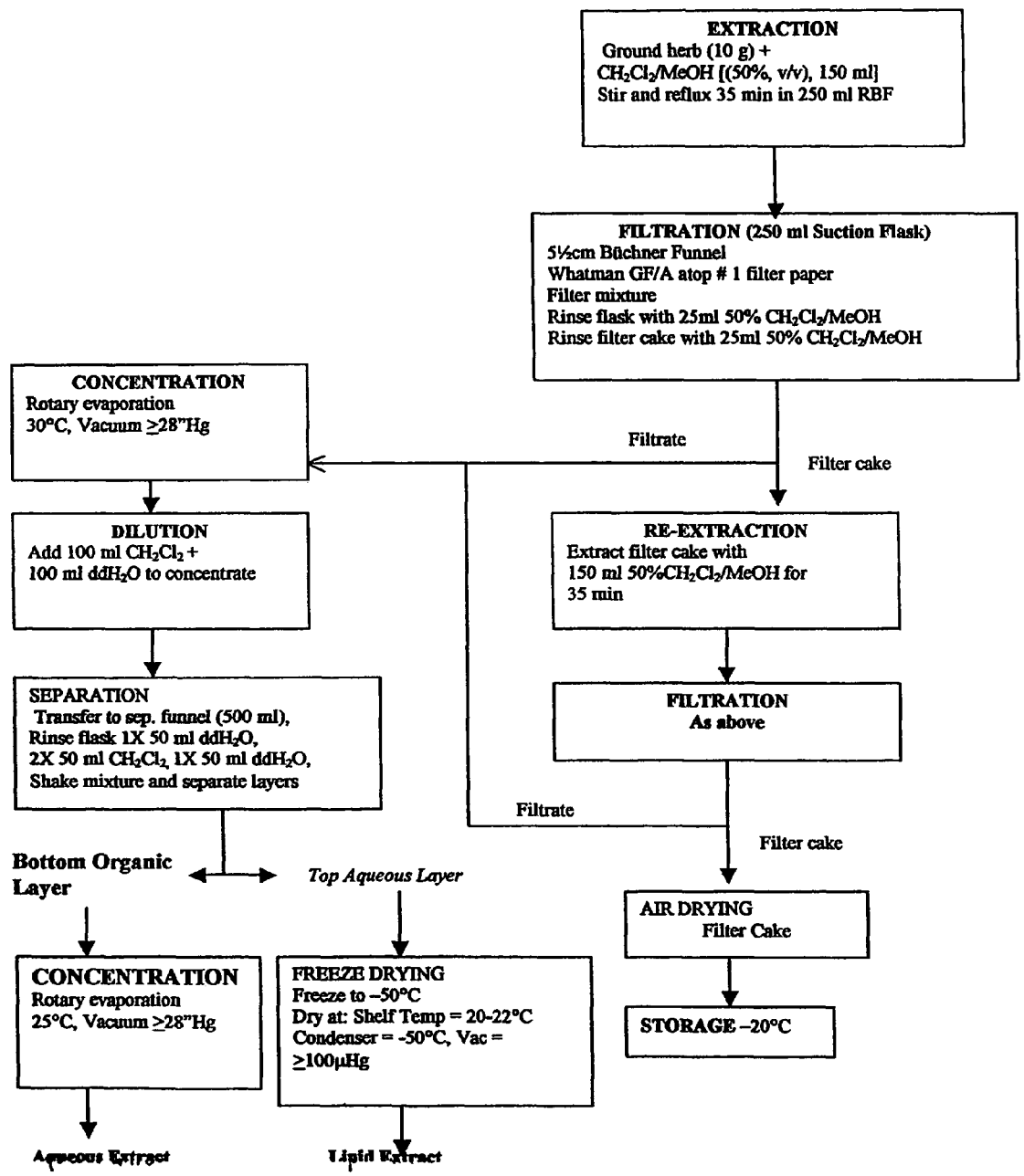

The present invention provides novel methods and compositions for use as anticancer agents for preventing and treating cancer in an individual. The present invention relates to a novel discovery that botanical extract-based compositions can effectively inhibit tumor growth and be substantially non-toxic when administered to an individual. The composition comprises extracts of *Ganoderma lucidum*, *Scutellaria barbata*, *Salvia miltiorrhiza*, and optionally, *Hippophae rhamnoides* (sea buckthorn)

In one embodiment, this method comprises administering a therapeutically effective amount of the composition to an individual (a mammal; and in a preferred embodiment, a human) bearing a tumor. In another embodiment, the method comprises administering a prophylactically effective amount of the composition to an individual to prevent tumor development (e.g., in an individual who is at high risk for developing tumor; or in an individual who is in remission, but at risk for recurrence).

Thus, a primary object of the present invention is to provide a method for treatment of a tumor bearing individual by administering a therapeutically effective and non-toxic amount of a composition having a property of inhibiting tumor growth when administered to the tumor bearing individual.

Another object of the present invention is to provide a method for prevention of tumor development in an individual at risk for tumor development by administering a prophylactically effective amount of a composition having a property of preventing or inhibiting the incidence of tumor growth when administered to the individual.

Another object of the present invention is to provide a method of treatment of a tumor bearing individual, or an individual at risk for developing tumor, with a therapeutically effective amount of a composition that has both properties of inhibiting tumor growth, and being substantially non-toxic when administered to the individual. "Substantially non-toxic" means that the composition lacks the toxicity generally associated with systemic chemotherapy; i.e., lacks detectable toxicities including hematologic, vascular, neural, gastrointestinal, renal, pulmonary, otologic, and immunosuppression (which may lead to lethal infections).

A further object of the present invention is to provide a method of treatment of an individual who has had a substantial reduction in tumor burden but who still is at risk for recurrence, wherein the method comprises administering to the individual a prophylactically effective amount of a composition that has both properties of inhibiting tumor growth, and being substantially non-toxic when administered to the individual.

Definitions

"Tumor" is used herein, for purposes of the specification and claims, to mean solid nonlymphoid primary tumor of ductal epithelial cell origin, including, but not limited to, tumors originating in the breast, prostate, colon, lung, pancreas, liver, stomach, bladder, or reproductive tract (cervix, ovaries, endometrium etc.), brain, and bone marrow; melanoma; or lymphoma.

"Inhibiting tumor growth" is used herein, for purposes of the specification and claims, to mean one or more of slowing the growth of the tumor, halting growth of the tumor, causing reduction or regression of the tumor, inhibiting tumor invasion, causing tumor cell death, and causing reduction or regression of metastases.

"Prevention of tumor development" is used herein, for purposes of the specification and claims, to mean inhibiting growth of the tumor; and more specifically, causing tumor cell death in preventing tumor mass formation.

The term "plant" as used herein refers to seeds, leaves, stems, flowers, roots, berries, bark, or any other plant parts that are useful for the purposes described. For certain uses, it is preferred that the underground portion of the plant, such as the root and rhizoma, be utilized. The leaves, stems, seeds, flowers, berries, bark, or other plant parts, also have medicinal effects and can be used for preparing tea and other beverages, cream, and in food preparation.

"Synergism" may be measured by combination index (CI). The combination index method was described by Chou and Talalay. (Chou, T.-C. The median-effect principle and the combination index for quantitation of synergism and antagonism, p. 61-102. In T.-C. Chou and D. C. Rideout (ed.), Synergism and antagonism in chemotherapy. Academic Press, San Diego, Calif. (1991); Chou, T.-C., and P. Talalay. Quantitative analysis of dose-effect relationships: the combined effects of multiple drugs on enzyme inhibitors. Adv. Enzyme Regul. 22:27-55 (1984)). A CI value of 0.90 or less is considered synergistic, with values of 0.85 being moderately synergistic and values below 0.70 being significantly synergistic. CI values of 0.90 to 1.10 are considered to be nearly additive and higher values are antagonistic.

TABLE 1

Synergism/antagonism as a function of CI values

| CI Value | Interpretation |
| --- | --- |
| >10 | Very strong antagonism |
| 3.3-10 | Strong antagonism |
| 1.45-3.3 | Antagonism |
| 1.2-1.45 | Moderate antagonism |
| 1.1-1.2 | Slight antagonism |
| 0.9-1.1 | Additive |
| 0.85-0.9 | Slight synergism |
| 0.7-0.85 | Moderate synergism |
| 0.3-0.7 | Synergism |
| 0.1-0.3 | Strong synergism |
| <0.1 | Very strong synergism |

It is noted that determination of synergy may be affected by biological variability, dosage, experimental conditions (temperature, pH, oxygen tension, etc.), treatment schedule and combination ratio. Synergism is measured as combination index (CI) values where values of 0.7 or less is considered to be significant levels of synergism.

Botanicals (i) *Ganoderma lucidum* (Reishi): *Ganoderma lucidum* was praised for its effect of increasing memory and preventing forgetfulness in old age reported in Shen Nong Ben Cao Jing vol. 1 as early as 456-536 AD. Research on mice using orally or topically administered *Ganoderma lucidum* suggests that *Ganoderma lucidum* has anti-inflammatory activity. Stavinoha, W., Satsangi, N., & Weintraub, S. (1995). Study of the antiinflammatory efficacy of *Ganoderma lucidum*. In B.-K. Kim, & Y. S. Kim (Eds.), Recent Advances in *Ganoderma lucidum* research (pp. 3-7). Seoul Korea: The Pharmaceutical Society of Korea.

Applications of *Ganoderma* for (1) chemoprophylaxis of cancer in individuals at high risk for developing cancer (2) adjuvent use in the prevention of metastasis or recurrence of cancer (3) palliation of cancer related cachexia and pain and (4) adjunctive use with concurrent chemotherapy to reduce side-effects, maintain leukocyte counts and allow a more optimal dosing of chemo or radio therapeutics has been suggested. Chang, R (1994) Effective Dose of *Ganoderma* in Humans; Proceedings of Contributed Symposium 59A, B 5th International Mycological Congress, Vancouver: pp. 117-121. Since studies of human dosage were traditional and empiric a proper dose range of *Ganoderma* for therapy was calculated using this data and pharmacokinetic principals. The calculations suggested that a (1) *Ganoderma* dried fruit body dose of 0.5 to 1 g per day for health maintenance (2) 2 to 5 g per day if there is chronic fatigue, stress, auto immune, or other chronic health problems (3) 5 to 10 g per day for serious illness. Chang, R (1993) Limitations and Potential applications of *Ganoderma* and related fungal polyglycans in clinical ontology; First International Conference on Mushroom Biology and Mushroom products: 96.

(ii) *Scutellaria barbata* (Skullcap): *Scutellaria barbata*, a traditional Chinese medicine for liver, lung and rectal tumours, has been shown to inhibit mutagenesis, DNA binding and metabolism of aflatoxin B1 (AFB1) and cytochrome P450-linked aminopyrine N-demethylase. (Wong B. Y., et al. Eur J Cancer Prev 1993 July; 2(4):351-6; Wong B. Y., et al., Mutat Res. 1992 Jun. 1; 279(3):209-16). *Scutellaria barbata* is also capable of enhancing macrophage function in vitro and inhibiting tumor growth in vivo. (Wong B. Y., et al. Cancer Biother Radiopharm 1996 February; 11(1):51-6).

This botanical contains vitamins C and E as well as calcium, potassium, magnesium, iron, zinc scutellarin, volatile oil, tannin and bitter principles. The scutellarin acts on the central nervous system. Scutellarin, an active ingredient from *Scutellaria barbata* has been purified by liquid chromatography. (Wenzhu Zhang; Duolong Di; Bo Wen; Xia Liu; Shengxiang Jiang, Determination of Scutellarin in *Scutellaria barbata* Extract by Liquid Chromatography-Electrochemical Detection, Journal of Liquid Chromatography & Related Technologies 26 (13): 2133-2140 (2003).

(iii) *Salvia miltiorrhiza* (Dan Shen): There are over 900 species of salvia and many of them have histories of medicinal uses. Dan shen is used in traditional Chinese medicine to promote blood circulation and to remove blood stasis. Bensky D, Gamble A Chinese botanical Medicine Materia Medica 1987 Eastland Press: Seattle. 384. It increases the activity of superoxide dismutase (SOD) in platelets, thus providing protection against pulmonary embolism and inhibition of platelet aggregation. Wang X, et al. "Effect of danshen injection on pulmonary thromboembolism and platelet free radical levels in mice". Zhongguo Zhong Yao Za Zhi 1996; 21:558-60. *Salvia miltiorrhiza* has been shown to lower cholesterol, reduce endothelial damage and to inhibit lipid peroxidation in hypercholesterolaemic animals. This inhibition of oxidation of LDL may reduce atherosclerosis. Wu Y J, et al. "Increase of vitamin E content in LDL and reduction of atherosclerosis in cholesterol-fed rabbits by a water-soluble antioxidant-rich fraction of *Salvia miltiorrhiza*." Arterioscler Thromb Vasc Biol 1998; 18:481-6. A Salvia miltiorrhiza constituent has been found to inhibit noradrenalineinduced contraction of the aortic strips through reduction in Ca2+ mobilization. This vasodilatory activity may explain the traditional use of *Salvia miltiorrhiza* in hypertension. Nagai M, et al. "Vasodilator effects of des (alpha-carboxy-3,4-dihydroxyphenethyl) lithospermic acid (8-epiblechnic acid), a derivative of lithospermic acids in salviae miltiorrhizae radix" Biol Pharm Bull 1996; 19:228-32. *Salvia miltiorrhiza* has been shown to have a markedly superior effect to nitroglycerin, with a more persistent action and better improvement of cardiac function. Bai Y R, Wang S Z. "Hemodynamic study on nitroglycerin compared with Salvia miltiorrhiza" Zhongguo Zhong Xi Yi Jie He Za Zhi 1994; 14:24-5, 4.

*Salvia miltiorrhiza* is also the top ingredient in Dan Shen Compound. Dan Shen Compound comprises four important botanicals for the improvement of peripheral circulation and general wellbeing. The actions of *Crataegus laevigata* are enhanced by the Chinese botanical *Salvia miltiorrhiza* (Dan Shen), the Indian botanical *Coleus forskohlii* and *Valeriana officinalis*. Chinese botanical medicine utilizes *Salvia miltiorrhiza* for women's irregularities, abdominal pain, insomnia, hives, hepatitis and mastitis.

(iv) *Hippophae rhamnoides* (sea buckthorn): Seabuckthorn seed oil contains a high content of the two essential fatty acids, linoleic acid and α-linolenic acid, which are precursors of other polyunsaturated fatty acids such as arachidonic and eicosapentaenoic acids. The oil from the pulp/peel of seabuckthorn berries is rich in palmitoleic acid and oleic acid (Chen et al. "Chemical composition and characteristics of seabuckthorn fruit and its oil." Chem. Ind. Forest Prod. (Chinese) 10 (3), 163-175). The increase in the level of a-linolenic acid in plasma lipids showed a clear improving effect on AD (atopic dermatitis) symptoms (Yang et al. J Nutr Biochem. 2000 Jun. 1; 11(6):338-340). These effects of α-linolenic acid may have been due to both changes in the eicosanoid composition and other mechanisms independent of eicosanoid synthesis (Kelley 1992, α-linolenic acid and immune response. Nutrition, 8 (3), 215-2).

Anti-oxidant and immunomodulatory properties of seabuckthorn (*Hippophae rhamnoides*) has been demonstrated using lymphocytes as a model system. (Geetha et al. J Ethnopharmacol 2002 March; 79(3):373-8). The antiulcerogenic effect of a hexane extract from *Hippophae rhamnoides* has also been demonstrated. (Suleyman H et al., Phytother Res 2001 November; 15(7):625-7). Radioprotection by a botanical preparation of *Hippophae rhamnoides* against whole body lethal irradiation in mice suggests free radical scavenging, acceleration of stem cell proliferation and immunostimulation properties. (Goel H C et al., Phytomedicine 2002 January; 9(1):15-25)

(v) *Camellia sinensis* (Green tea): Dried leaves from the *Camellia sinensis* plant is processed into three types of tea: oolong tea, black tea, and green tea. Green tea extract is a bioflavonoid-rich, potent extract which is used primarily for fighting free radicals. It has a high content of polyphenols, which are a Type of bioflavonoids. In making green tea, the tea leaves are stabilized by moist or dry heat which destroys the enzyme polyphenoloxidase and thus, prevents oxidation of polyphenols. These polyphenols are the main biologically active ingredients in green tea. In preferred embodiments, the green tea is Dragon Well tea or Lung Ching tea.

The polyphenols in green tea are catechins, with multiple linked ring-like structures. Polyphenols are a form of bioflavonoids with several phenol groups. They control both taste and biological action. Catechins, a chemical group of polyphenols possessing antioxidant properties (protecting cells from free radical-mediated damage), include epigallocatechin-3 gallate (EGCG), epigallocatechin, and epicatechin-3-gallate. Recently, ECGC has been shown to be an inhibitor of urokinase (Jankun et al., 1997, Nature 387:561), and quinol-oxidase; enzymes that may be crucial for growth of tumor cells. Epigallocatechin-3 gallate (EGCG) also protects against digestive and respiratory infections.

*Ganoderma lucidum, Scutellaria barbata, Salvia miltiorrhiza*, and *Hippophae rhamnoides* (sea buckthorn), and *Camellia sinensis* (green tea) have been used individually for health promoting and therapeutic purposes. Novel tumor inhibiting, immune boosting, inflammation reducing and anti-oxidative properties observed for compositions comprising extracts of *Ganoderma lucidum, Scutellaria* barbata, Salvia miltiorrhiza, and, optionally, *Hippophae rhamnoides* (sea buckthorn), and *Camellia sinensis* (green tea) and the synergistic effects demonstrated by novel combinations of two or more of these extracts used in the method according to the present invention are a likely result of combinations of one or more of saponins, flavonoids and polyphenols present in the extracts.

Compositions

The compositions are standardized based on specific activities of defined properties which allows for very effective quality control based on standardized $IC_{50}$ based combinations. As discussed elsewhere in this application specific extraction procedures further facilitate the standardization of the compositions.

The compositions comprise botanical preparations extracted with hot water and organic solvents which allow convenient (e.g., oral) drug delivery.

The compositions of the present invention can be in any form which is effective, including, but not limited to dry powders, grounds, emulsions, extracts, and other conventional compositions. To extract or concentrate the effective ingredients of The compositions, typically the plant part is contacted with a suitable solvent, such as water, alcohol, methanol, or any other solvents, or mixed solvents. The choice of the solvent can be made routinely, e.g., based on the properties of the active ingredient that is to be extracted or concentrated by the solvent. Preferred active ingredients of The compositions crenulata include, but are not limited to, salidroside, tyrosol, β-sitosterol, gallic acid, pyrogallol, crenulatin, rhodionin, and/or rhodiosin. These ingredients can be extracted in the same step, e.g., using an alcoholic solvent, or they may be extracted individually, each time using a solvent which is especially effective for extracting the particular target ingredient from the plant. In certain embodiments, extraction can be performed by the following process: Milling the selected part, preferably root, to powder. The powder can be soaked in a desired solvent for an amount of time effective to extract the active agents from the The compositions. The solution can be filtered and concentrated to produce a paste that contains a high concentration of the constituents extracted by the solvent. In some cases, the paste can be dried to produce a powder extract of The compositions crenulata. The content of active ingredient in the extract can be measured using HPLC, UV and other spectrometry methods.

The compositions of the present invention can be administered in any form by any effective route, including, e.g., oral, parenteral, enteral, intraperitoneal, topical, transdermal (e.g., using any standard patch), ophthalmic, nasally, local, non-oral, such as aerosal, inhalation, subcutaneous, intramuscular, buccal, sublingual, rectal, vaginal, intra-arterial, and intrathecal, etc. It can be administered alone, or in combination with any ingredient(s), active or inactive, including in a medicinal form, or as a food or beverage additive.

In preferred embodiments of the invention, the compositions are administered orally in any suitable form, including, e.g., whole plant, powdered or pulverized plant material, extract, pill, capsule, granule, tablet or a suspension.

The compositions can be combined with any pharmaceutically acceptable carrier. By the phrase, "pharmaceutically acceptable carriers," it is meant any pharmaceutical carrier, such as the standard carriers described, e.g., Remington's Pharmaceutical Science, 18th Edition, Mack Publishing company, 1990. Examples of suitable carriers are well known in the art and can include, but are not limited to, any of the standard pharmaceutical carriers such as a phosphate buffered saline solutions, phosphate buffered saline containing Polysorbate 80 (TWEEN® 80; Polyoxyethylene-sorbitan-monooleate), water, emulsions such as oil/water emulsion and various type of wetting agents. Other carriers may also include sterile solutions, tablets, coated tablets pharmaceutical and capsules. Typically such carriers contain excipients such as such as starch, milk, sugar, certain types of clay, gelatin, stearic acid or salts thereof, magnesium or calcium stearate, talc, vegetable fats or oils, gums, glycols. Such carriers can also include flavor and color additives or other ingredients. Compositions comprising such carriers are formulated by well known conventional methods. Generally excipients formulated with the compositions are suitable for oral administration and do not deleteriously react with it, or other active components.

Suitable pharmaceutically acceptable carriers include but are not limited to water, salt solutions, alcohols, gum arabic, vegetable oils, benzyl alcohols, gelatin, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose and the like. Other additives include, e.g., antioxidants and preservatives, coloring, flavoring and diluting agents, emulsifying and suspending agents, such as acacia, agar, alginic acid, sodium alginate, bentonite, carbomer, carrageenan, carboxymethylcellulose, cellulose, cholesterol, gelatin, hydroxyethyl cellulose, hydroxppropyl cellulose, hydroxypropyl methylcellulose, methylcellulose, octoxynol 9, oleyl alcohol, povidone, propylene glycol monostearate, sodium lauryl sulfate, sorbitan esters, stearyl alcohol, tragacanth, xanthan gum, and derivatives thereof, solvents, and miscellaneous ingredients such as microcrystalline cellulose, citric acid, dextrin, dextrose, liquid glucose, lactic acid, lactose, magnesium chloride, potassium metaphosphate, starch, and the like.

The compositions can also be formulated with other active ingredients, such as anti-oxidants, vitamins (A, C, ascorbic acid, B's, such as B1, thiamine, B6, pyridoxine, B complex, biotin, choline, nicotinic acid, pantothenic acid, B12, cyanocobalamin, and/or B2, D, D2, D3, calciferol, E, such as tocopherol, riboflavin, K, K1, K2). Preferred compounds, include, e.g. creatine monohydrate, pyruvate, L-Carnitine, α-lipoic acid, Phytin or Phytic acid, Co Enzyme Q10, NADH (nicotinamide adenine dinucleotide hydride), NAD (nicotinamide adenine dinucleotide), D-ribose, amino acids such as L-glutamine, Lysine, chrysin; pre-hormones such as 4-androstenedione, 5-androstenedione, 4(or 5-)androstenediol, 19-nor-4 (or 5-)-androstenedione, 19-nor-4 (or 5-)-androstenediol, Beta-ecdysterone, and 5-Methyl-7-Methoxy Isoflavone. Preferred active ingredients include, e.g., pine pollen, *Fructus lycii, Hippophae rhamnoides, Ligusticum, Acanthopanax, Astragalus, Ephedra, Codonopsis, Polygala tenuifolia* Wild, *Lilium, Sparganium,* ginseng, *Panax notogiseng, Garcinia, Guggle,* Grape Seed Extract or powder, and/or *Ginkgo biloba.*

Other plants and botanicals which can be formulated with the compositions of the present invention includes those mentioned in various text and publications, e.g., ES Ayensu, Medicinal Plants of West Africa, Reference Publications, Algonac, Mich. (1978); L. Boulos, Medicinal Plants of North Africa, Reference Publications Inc., Algonac, Mich. (1983); and N. C. Shah, Botanical Folk Medicines in Northern India, J. Ethnopharm, 6:294-295 (1982).

Other active agents include, e.g., antioxidants, anti-carcinogens, anti-inflammatory agents, hormones and hormone antagonists, antibiotics (e.g., amoxicillin) and other bacterial agents, and other medically useful drugs such as those identified in, e.g., Remington's Pharmaceutical Sciences, 18th Edition, Mack Publishing Company, 1990. A preferred composition of the present invention comprises, about 1%-100%, preferably about 20-70% of the botanical extract; and, optionally, a pharmaceutically-acceptable excipient.

The present invention relates to methods of administering the compositions, e.g., to provide antioxidant effects, to protect against oxidation, to provide anti-cancer effects, to promote DNA repair, to provide anti-radiation effects, to protect against radiation, to reduce inflammation, and other conditions and diseases as mentioned herein.

By the term "administering," it is meant that the compositions are delivered to the host in such a manner that it can achieve the desired purpose. As mentioned The compositions can be administered by an effective route, such as orally, topically, rectally, etc. The compositions can be administered to any host in need of treatment, e.g., vertebrates, such as mammals, including humans, male humans, female humans, primates, pets, such as cats and dogs, livestock, such as cows, horses, birds, chickens, etc.

An effective amount of the compositions are administered to such a host. Effective amounts are such amounts which are useful to achieve the desired effect, preferably a beneficial or therapeutic effect as described above. Such amount can be determined routinely, e.g., by performing a dose-response experiment in which varying doses are administered to cells, tissues, animal models (such as rats or mice in maze-testing, swimming tests, toxicity tests, memory tests as performed by standard psychological testing, etc.) to determine an effective amount in achieving an effect. Amounts are selected based on various factors, including the milieu to which the virus is administered (e.g., a patient with cancer, animal model, tissue culture cells, etc.), the site of the cells to be treated, the age, health, gender, and weight of a patient or animal to be treated, etc. Useful amounts include, 10 milligrams-100 grams, preferably, e.g., 100 milligrams-10 grams, 250 milligrams-2.5 grams, 1 gm, 2 gm, 3 gm, 500 milligrams-1.25 grams. etc., per dosage of different forms of the compositions such as the botanical powder, botanical extract paste or powder, tea and beverages prepared to contain the effective ingredients of the compositions, and injections, depending upon the need of the recipients and the method of preparation.

Cytostatic Compositions

The cytostatic compositions of this invention are also referred to as ANEUSTAT™.

Compositions of the present invention comprise effective amounts of extracts of *Ganoderma lucidum, Scutellaria barbata, Salvia miltiorrhiza*, and, optionally, *Hippophae rhamnoides* (sea buckthorn) that exhibit cytostatic effects for use in inhibiting further growth of pre-existing cancer cells by exhibiting one or more properties of (i) boosting the immune system, (ii) reducing oxidative damage to cells and tissues, (iii) reducing inflammation, (iv) arresting proliferation of cells in certain stages of the cell cycle, (v) anti-oxidant activity, and (vi) anti-mutagenic effects against further exposure to carcinogens and mutagens.

In one aspect of the invention, the composition comprises equal amounts of extracts of *Ganoderma lucidum, Scutellaria barbata*, and *Salvia miltiorrhiza*. The dosage of the composition can be readily determined by one of skill in the art based on the effective concentrations of compositions shown to display the various properties described in this application. Compositions comprising different ratios of the individual extracts can similarly be determined.

Cytotoxic Compositions

The cytotoxic compositions of this invention are also referred to as ANEUTOX™.

The compositions of the present invention comprise extracts of *Ganoderma lucidum, Scutellaria barbata, Salvia miltiorrhiza*, and, optionally, *Hippophae rhamnoides* (sea buckthorn) that are useful in cytotoxic compositions to be administered in conjunction with chemotherapeutic agents, radiation treatment and surgery. These compositions exhibit one or more properties of (a) synergistic action with chemotherapy (increasing sensitivity to chemotherapeutic agents), (b) synergistic action with radiation therapy and surgery (increasing effectiveness by inhibiting growth of pre-existing cancer cells that are missed by radiation or surgery) in addition to the previously stated properties of (i) boosting the immune system, (ii) reducing oxidative damage to cells and tissues, (iii) reducing inflammation, (iv) arresing proliferation of cells in certain stages of the cell cycle, (v) anti-oxidant activity, and (vi) anti-mutagenic effects against furtjer exposure to carcinogens and mutagens. Anti-mutagenic properties (together with increased sensitivity by synergism) reduce levels of chemotherapeutic agents necessary for treatment thus resulting in reduced toxicity for patients.

The cytotoxic compositions of the present invention may be used in conjunction with chemotherapeutic agents including alkylating agents, antimetabolites antagonists, anticancer antibiotics, and plant-derived anticancer agents.

Examples of "alkylating agents" include nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, carboquone, adozelesin, cystemustine, and bizelesin.

Examples of "antimetabolites" include mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emmitefur), aminopterine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, and ambamustine, etc.

Examples of "anticancer antibiotics" include actinomycin-D, actinomycin-C, mitomycin-C, chromomycin-A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, and idarubicin hydrochloride, etc.

Examples of "plant-derived anticancer agents" include etoposide phosphate, vinblastine sulfate, vincristine sulfate, vindesine sulfate, teniposide, paclitaxel, docetaxel, and vinorelbine, etc.

The cytotoxic compositions of the present invention may also be used in conjunction with immunotherapeutic agents including picibanil, krestin, sizofuran, lentinan, ubenimex, interferons, interleukins, macrophage colony-stimulating factor, granulocyte colony-stimulating factor, erythropoietin, lymphotoxin, BCG (Bacille Calmette Guerin) vaccine, *Corynebacterium parvum*, levamisole, polysaccharide K, and procodazole.

The compositions are selected from combinations of extracts comprising two or more of *Ganoderma lucidum, Scutellaria barbata*, and *Salvia miltiorrhiza*. Combinations of these compounds are shown to synergistically inhibit proliferation of cancer cells (including cervical and lung cancer cells). Extracts of the individual botanicals are found to also reduce oxidation, reduce inflammation and boost the immune system.

In one aspect of the invention, the composition comprises equal amounts of extracts of *Ganoderma lucidum, Scutellaria barbata*, and *Salvia miltiorrhiza*. The dosage of the composition can be readily determined by one of skill in the art based on the effective concentrations of compositions shown to display the various properties described in this application. Compositions comprising different ratios of the individual extracts can similarly be determined. For example, a composition may exhibit cytostatic effects at one concentration or ratios of combinations of extracts and varying degrees of cytotoxic effects at other concentrations or ratios of combinations of extracts.

In one embodiment, anticancer therapy comprises administering to an individual at risk of developing a cancer, a prophylactically effective amount of the compositions of the invention. A prophylactically effective amount is an amount that can effect cancer inhibition when administered to an individual at risk of developing a cancer (new cancer or recurrence). As known to those skilled in the art, the dosage may vary with the individual depending on the age, size, health, and metabolism of the individual, and related factors. The route of administration may be by any conventional route in which the composition can be safely and effectively delivered. A preferred route of administration is an oral route. The composition may be administered in tablet/caplet/capsule form, or in a form in a pharmaceutically acceptable carrier (e.g., liquid, water, saline or other physiological solution, or gel).

Combinations of extracts comprising two or more of *Ganoderma lucidum, Scutellaria barbata*, and *Salvia miltiorrhiza* are selected for the abilities to inhibit proliferation of cancer cells (including cervical and lung cancer cells), reduce oxidation, reduce inflammation and boost the immune system. In addition, other anticancer compounds (chemotherapeutic agents) are included in a typical composition.

Chemotherapeutic agents suitable for use in the compositions and methods of the present invention may be any known pharmaceutically acceptable agent that depends, at least in part, on interfering with cellular structure and/or metabolism for its anticancer activity. Examples of conventional chemotherapeutic agents include, but are not limited to, platinum compounds such as cisplatin, carboplatin and their analogs and derivatives; alkylating agents such as chlorambucil, nitrogen mustards, nitromin, cyclophosphamide, 4-hydroperoxycyclophosphamide; 2-hexenopyranoside of aldophosphamide, melphalan, BCNU (β-chloro-nitrosourea), CCNU (N-(2-chloroethyl)-N'-cyclohexyl-N-nitroso-urea), methyl-CCNU (methyl-N-(2-chloroethyl)-N'-cyclohexyl-N-nitrosourea), uracil mustard, mannomustine, triethylenemelamine, chlorozotocin, ACNU (3-[(4-amino-2-methyl-5-pyrimidinyl)methyl]-1-(2-chloroethyl)-1-nitrosourea), GANU (1-(2-chloroethyl) 1-nitroso-3-fl-(D-gluco-pyranosyl)urea), MCNU (1-(2-chloroethyl)-1-nitroso-3-[(3,4,5-trihydroxy-6-methoxy-oxan-2-yl)methyl]urea), TA-77 (3-(β-D-glucopyranosyl)-1-(2-chloroethyl)-1-nitrosourea ranimustine), hexamethylmelamine, dibromomannitol, pipobroman, epoxypropidine, epoxypiperazine, ethoglucide, pippsulfan, dimethylmilelane, bubulfan, inprocuon, threnimone, thio-TEPA (N,N'N'-triethylenethiophosphoramide) and Aza-TEPA (P,P-Bis(aziridin-1-yl)-N-ethyl-N-1,3,4-thiadiazol-2-ylphosphinamide); antimetabolites such as 5-fluorouracil, folic acid, methotrexate (MTX), 6-mercaptopurine, aminopterin, 8-azaguanine, azathioprine, uracil, cytarabine, azaserine, tegaful, BHAC (behenoyl cytosine arabinoside), SALVIA MILTIORRHIZA108 (*Salvia miltiorrhiza* 108), cytosine arabinoside, cispuracham, diazamycine, HCFU (1-Hexylcarbamoyl-5-Fluorouracil), 5'DFUR (5'-deoxy-5-fluorouridine), TK-177 and cyclotidine; antibiotics such as bleomycin, daunomycin, cyclomycin, actinomycin D, mitomycin C, carzinophylin, macrocinomycin, neothramycin, macromomycin, nogaromycin, cromomycin, 7-o-methyl-nogallol-4'-epiadriamycin,4-demethoxydaunorubicin, streptozotocin (STZ), DON (deoxynorleucine) and mitozanthron; bis-chloroethylating agents, such as mafosamide, nitrogen mustard, nornitrogen mustard, melphalan, chlorambucil; hormones such as estrogens; bioreductive agents such as mitomycin C and others such as mitoxantrone, procarbazine, adriblastin, epirubicin, prednimustine, ifosfamid, P-glycoprotein inhibitors such as thaliblastine and protein kinase inhibitors such as protein kinase C inhibitor (ilmofosine). Chemotherapeutic agents particularly refer to the antimicrotubule agents or tubulin targeting agents including vinca alkaloids; vinca alkaloids such as etoposide, podophyllotoxin, vincristine and vinblastine; taxanes (paclitaxel, docetaxel and precursor taxane (10-deacetylbaccatin III), arsenic salts, colchicin (e), thio-colchicine, coichiceine, colchisal and other colchium salts; epipodophyllotoxins (etoposide), cytochalasins (such as A-E, H, J), okadaic acid, carbaryl and it's metabolites such as naphthol or naphthyl compounds including 1-naphthol, 2-naphthol, 1-naphthylphosphate, malonate, nocodazole (methyl-(5-[2-thienyl-carbonyl]-1H-benzimidazol-2-yl)carbamate), cryptophycin (CP) and its analogues such as CP-52, wortmannin, 12-O-tetradecanoylphorbol-13-acetate (TPA), 14-3-3 sigma and its homologs (such as rad24 and rad25), Ustiloxin F, monocrotalines such as monocrotaline pyrrole (MCTP), estramustine and the inhibiting agents of adenosine. These chemotherapeutic agents may be used either alone or in combination. Preferably, one antimetabolite and one antimicrotubule agent are combined, and more preferably taxol, cisplatin, chlorambucil, cyclophosphamide, bleomycin, or 5-fluorouracil which have different tumor killing mechanisms are combined. The combination containing arsenic compounds, colchicin, colchicine, colchiceine, colchisal, colchium salts, vinblastine, paclitaxel and related compounds that interfere with the cytoskeletons are most preferred. As new chemotherapeutic agents and drugs are identified and become available to the art, they may be directly applied to the practice of the present invention.

In a preferred embodiment, an all natural Cytotoxic composition comprises plant components such as cyclophosphamide, 4-hydroperoxycyclophosphamide, thiotepa, taxol and related compounds, doxorubicin, daunorubicin and neocarzinostain in addition to any two or more of *Ganoderma lucidum, Scutellaria barbata*, and *Salvia miltiorrhiza*.

Drugs that are currently used in cancer therapy and designed to perturb microtubule shortening (depolymerization) or lengthening (polymerization) such as paclitaxel, docetaxel, etoposide, vincristine, vinblastine, and vinorelbine are a preferred component of cytotoxic compositions. These drugs bind to tubulin, the molecule of which microtubules are composed, and arrest cells in mitosis by inhibiting spindle assembly (Compton, D. A., et al., (1999) Science 286:313-314).

The methods according to the present invention for anti-cancer therapy with cytotoxic compositions further comprises administering a therapeutically effective amount of one or more standard anticancer treatments (e.g., one or more of radiation therapy, chemotherapy, surgery, immunotherapy, and photodynamic therapy) in addition to administering a therapeutically effective amount of the composition. In a preferred embodiment of this alternative, the method comprises administering a therapeutically effective amount of one or more standard chemotherapeutic drugs in addition to administering a therapeutically effective amount of the composition. A combination of a therapeutically effective amount of one or more standard chemotherapeutic drugs and a therapeutically effective amount of the cytotoxic composition, can result in a synergistic effect in tumor inhibition (including regression of existing tumor).

Properties

Several distinct properties of the compositions of this inventions make them uniquely suitable in cancer therapy.

The botanical sources of the extracts are natural compounds are essentially non-toxic with a long history of usage of the individual compounds/extracts. Anti-mutagenic properties as evidenced by Ames test results (together with increased sensitivity by synergism) reduce levels of chemotherapeutic agents necessary for treatment resulting in reduced toxicity for patients.

The compositions also demonstrate the ability to enhanced cell cycling which could make the composition of ANEUSTAT™ a powerful adjuvant to chemotherapy (in an ANEUTOX™ formulation) or radiation therapy by increasing effectiveness and reducing dosage of chemotherapeutic agents.

Quality control. $IC_{50}$ based compositions can be standardized based on specific activities of defined properties.

The compositions are also suited for convenient (oral) drug delivery. Compositions extracted with hot water and organic solvents (ethyla acetate ester, ethanol).

Overall the compositions show mostly cytostatic effect with very weak cytotoxic effects in the Aneustat composition. Cytotoxic compositions (Aneutox) optionally include known chemotherapeutic agents.

The compositions demonstrate anti-oxidant activity which prevents damage to chromosomes/genes, reduces effect of mutagens, alleviates side-effects of chemotherapeutic agents, and enhances cell repair mechanisms.

The compositions further demonstrate immune system boosting activity which facilitates elimination of (i) damaged cells or (ii) cells with damaged genes. Further, the compositions provide general benefits of improving immune condition (passive immunotherapy).

Histopathology of ANEUSTAT™-treated cells indicates minimal retention of dead cancer cells which enhance recovery following cancer therapy.

The composition shows marked anti-inflammation activity. ANEUSTAT™ shows Cox-2 inhibition (in preference over COX-1 by over 4.5×). This activity retards tumor progression as COX-2 inhibitors have been suggested as means for treating cancer.

ANEUSTAT™ also induces lymphocytes to release tumor necrosis factor alpha which is known to play a significant role in facilitating apoptosis which is critical in cancer therapy.

Thus the ANEUSTAT™ composition is useful in prevention of cancer as well as inhibiting growth of existing cancer cells. The ANEUTOX™ composition can be used in combination with chemotherapeutic agents. It reduces drug resistance as well as acts as an adjuvant to chemotherapy, radiation and surgery. Further, the composition acts synergistically with the cancer therapies: chemotherapy, radiation therapy and surgery, thus enhancing effectiveness and reducing required dosage levels. Finally, the composition is unique and effective because the effects of the individual components of the composition act synergistically.

EXAMPLES

Without further elaboration, it is believed that one skilled in the art can, using the preceding description, utilize the present invention to its fullest extent. The following examples are illustrative only, and not limiting of the remainder of the disclosure in any way whatsoever.

The following combinations of extracts were used throughout the examples: *Ganoderma lucidum, Scutellaria barbata*, and *Salvia miltiorrhiza* are the components of Aneustat. Aneutox comprises the same components in the same or different concentrations and additionally comprises, optionally, a chemotherapeutic agent.

In addition, the compositions of the invention may include, optionally, *Panax quinquefolium* (Western ginseng), *Camellia sinensis* (green tea), and *Hippophae rhamnoides* (sea buckthorn). Results obtained with these combinations or the individual extracts were often compared with ACAPHA, a combination of six botanicals (*Sophora tonkinensis, Polygonum bistorta, Prunella vulgaris, Sonchus brachyotus, Dictamnus dasycarpus* and *Dioscorea bulbifera*).

Example 1

Methods for Preparation of Botanical Extracts

The compositions of the present invention may be administered as dried botanicals. Botanical preparations contain phytochemicals some of which are soluble in aqueous media while others are relatively more soluble in organic (alcohol, lipid) media. Different extraction methods were used and tested for the ability to extract effective ingredients from the botanicals. Extraction methods include: Hot Water extraction; Organic (lipid fraction) extraction; Organic (aqueous fraction) extraction; and Ethanol Extraction.

Products are prepared from botanicals using different solvents by the general extraction platform shown in FIG. 1A. In general, the botanicals are pre-screened for uniform size and quality by visual and other inspection means. The raw botanical material is extracted with the desired solvent. Preferably, the extraction process is carried out twice for each batch. The liquid extracts are evaporated to dryness. If needed, the solvent is removed and the dried extracts are blended as the final products. Optionally, the blends may be encapsulated for storage and delivery.

Figure 1E:
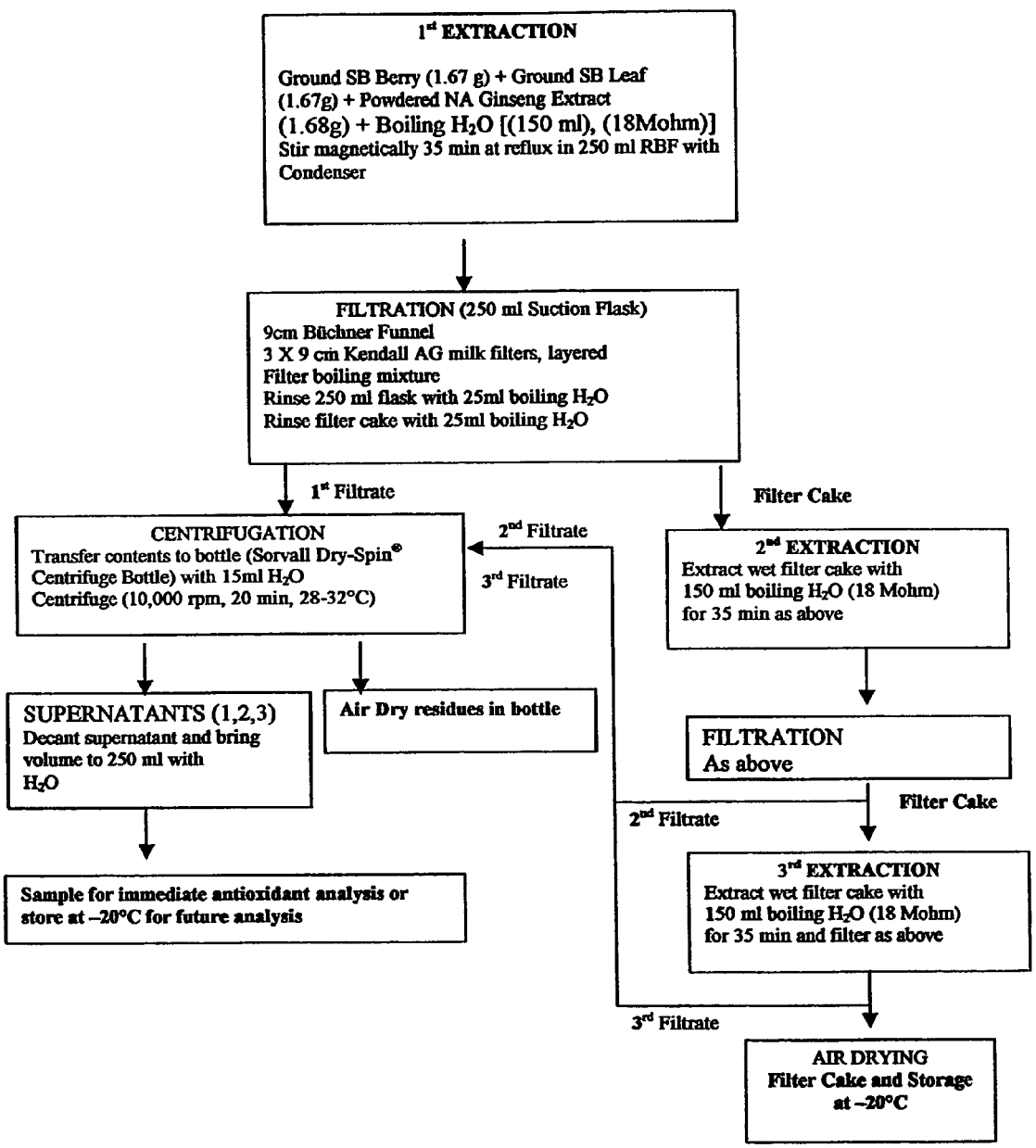
Figure 1F:
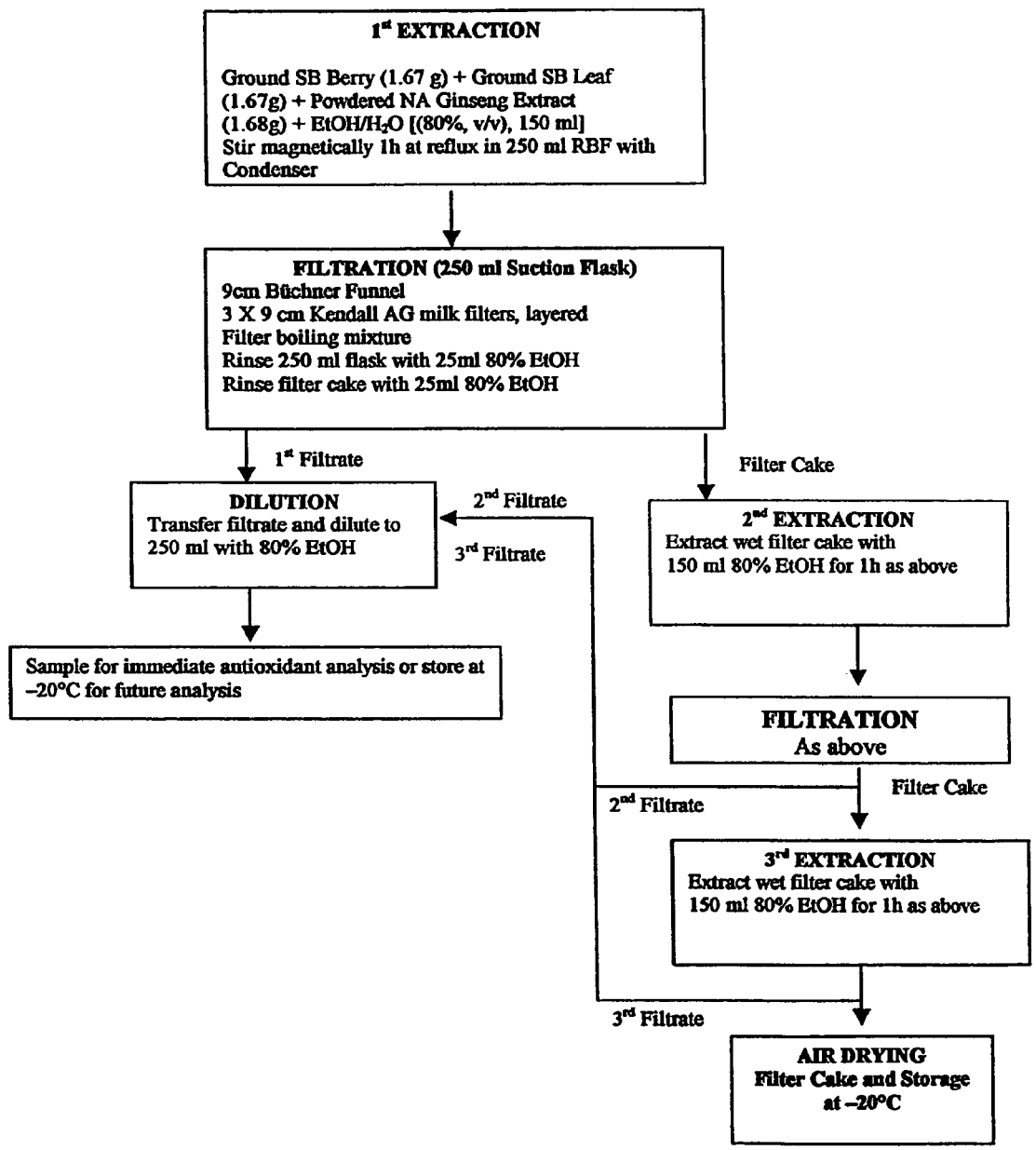
Figure 1G:
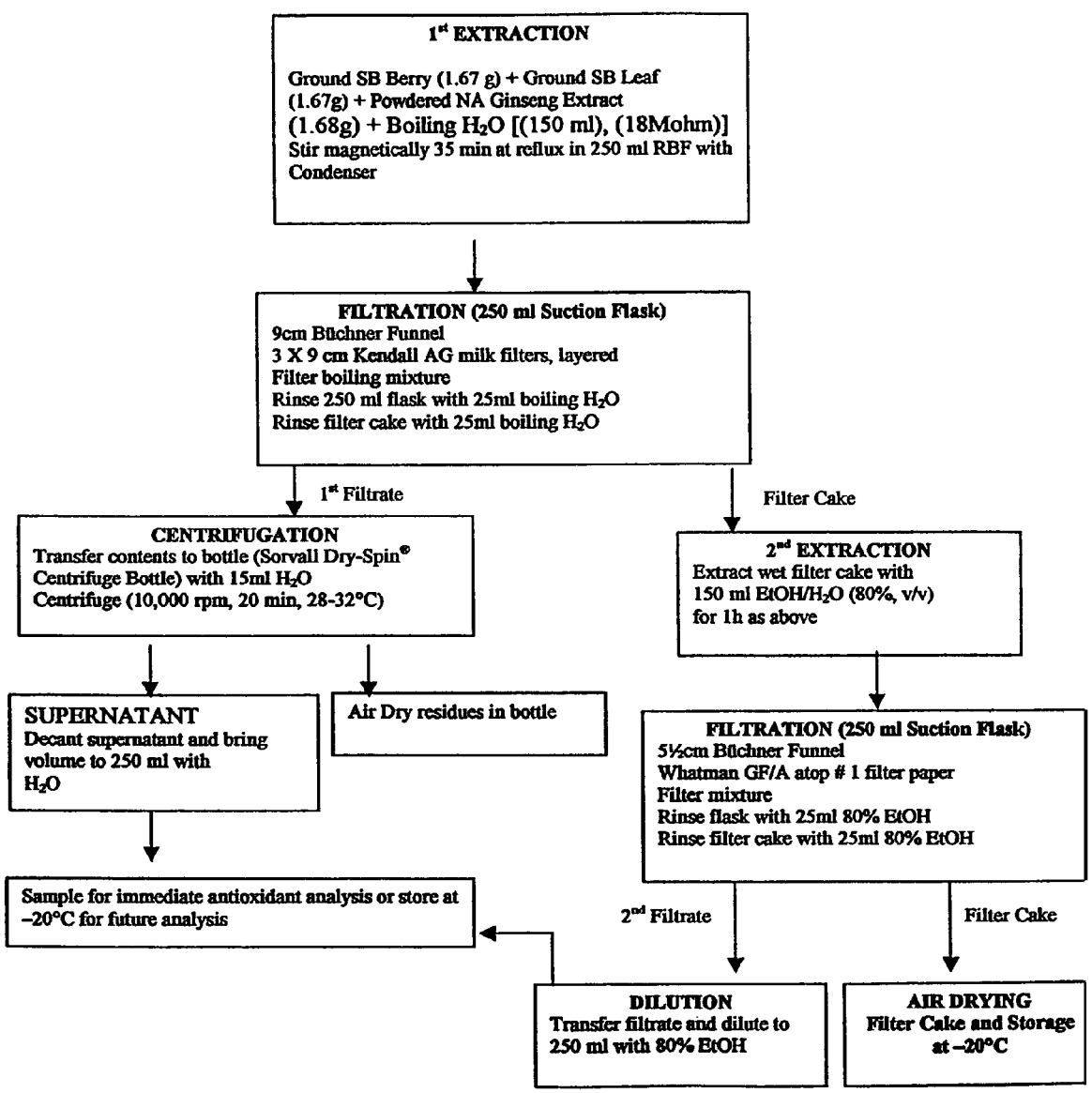
Figure 1H:
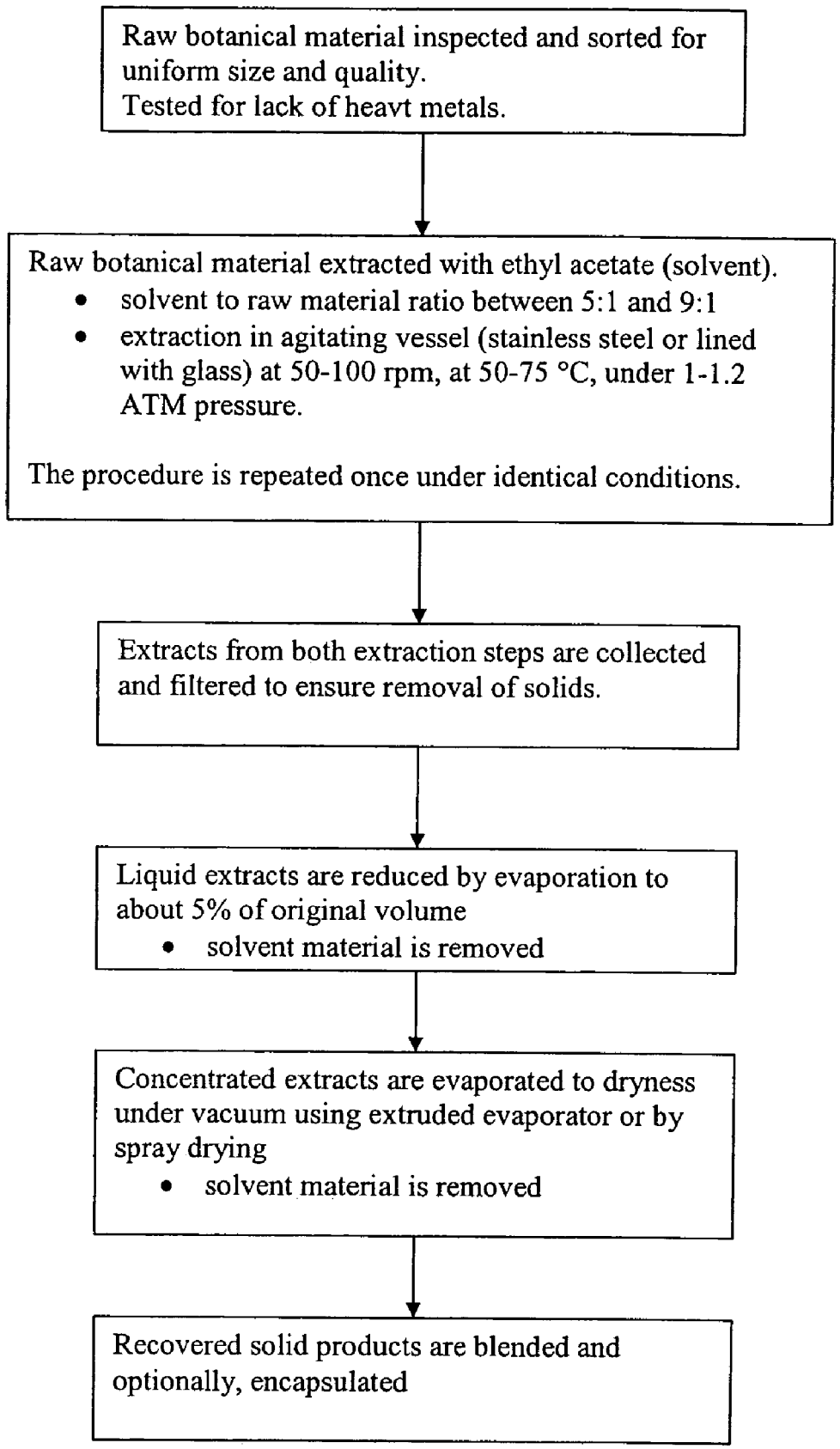

In the extraction schemes depicted in FIGS. 1B-1G, botanical or botanical blends were extracted with solvent (hot water, 80% ethanol, or ethyl acetate) under reflux for 30-60 minutes, separated by filtration to obtain a filtrate, and air dried for further analysis. The filtrates were combined, diluted or concentrated prior to determination of activities. Extraction procedures with hot water, 80% ethanol and chloroform/methanol are shown schematically in FIGS. 1B, 1C, and 1D respectively. Extraction procedures of botanical blends with hot water, 80% ethanol and hot water followed by 80% ethanol are illustrated in FIGS. 1E, 1F and 1G respectively. Extraction procedure of botanical blends with ethyl acetate is illustrated in FIG. 1H.

Example 2

A large range of concentrations (in mg/ml) of individual botanical extracts of *Ganoderma lucidum, Scutellaria barbata*, Pq (*Panax quinquefolium*) and *Salvia miltiorrhiza* required for the inhibition of cancer cell proliferation in A549 human lung cancer cells in tissue culture were tested for a duration of 72 h. The increase in cell number in the presence and absence of extract was measured by Sulforhodamine B assay. $IC_{50}$ values for inhibition of cell growth were obtained by measuring the amount of total cell protein with the sulforhodamine B assay as described by Skehan et al., New Colorimetric Cytotoxicity Assay for Anticancer-drug Screening," J. Natl. Cancer Inst., 82:1107-1112 (1990). MCF-7 cells were grown in RPMI 1640 medium containing 17% fetal calf serum, 12 μg/mL gentamicin sulfate and 2 mM glutamine at 37° in 5% $CO_2$. Confluent cells were trypsinized, diluted 40-fold, and seeded into 96-well microtiter plates. After 24 hours of growth without drug, medium with varying concentrations of drug was added to different wells (final concentration of dimethyl sulfoxide, 0.1%). $IC_{50}$ values were determined after an additional 48 hours.

Figure 2:
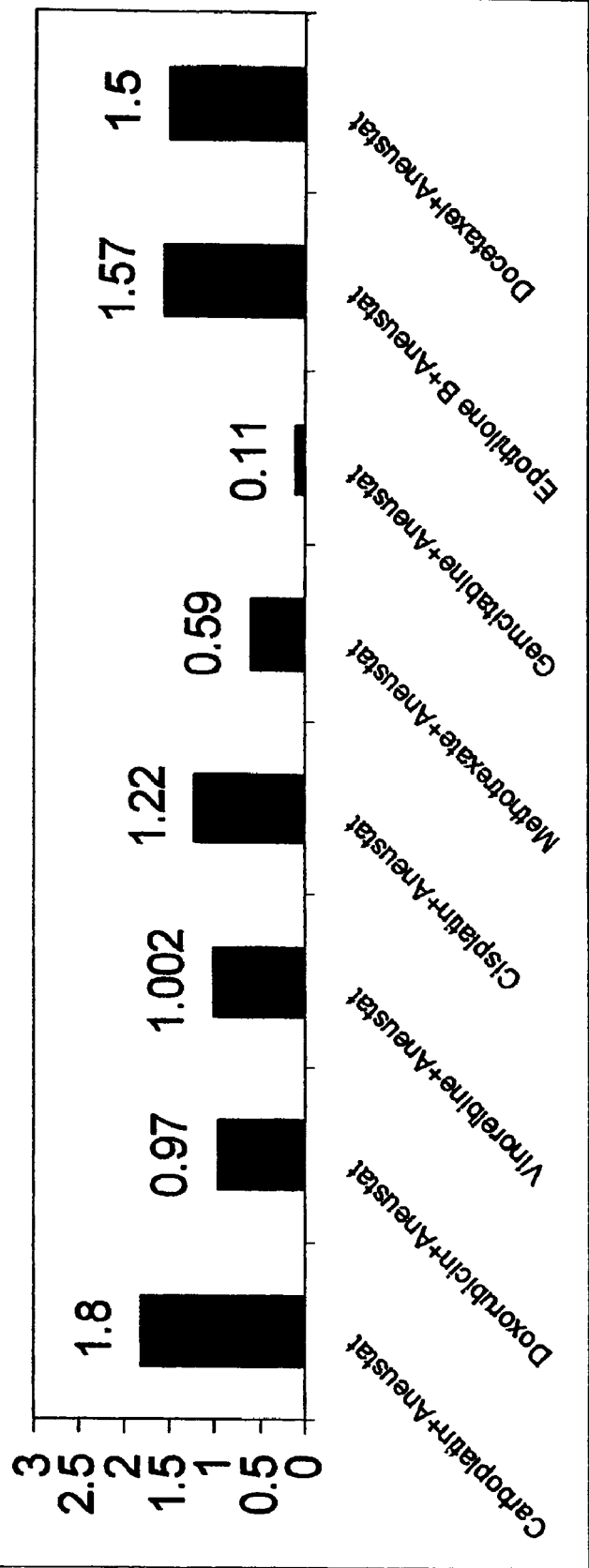
FIG. 2 shows combination index (CI) values for inhibition of cell proliferation on compositions (ANEUSTAT™) comprising *Ganoderma lucidum* (#8), *Scutellaria barbata* (#15), and *Salvia miltiorrhiza* (#14) and chemotherapeutic drugs.

FIG. 2 shows combination index (CI) values for inhibition of cell proliferation on compositions (ANEUSTAT™) comprising *Ganoderma lucidum* (#8), *Scutellaria barbata* (#15), and *Salvia miltiorrhiza* (#14) and chemotherapeutic drugs. Each component was added to a concentration of their respective $IC_{50}$ values. ANEUSTAT™ showed highly significant and strong synergy with Gemcitabine (GEMZAR®) and significant synergy with methotrexate. Some antagonism was noted with carboplatin, epothilone B and docetaxel (TAXOTERE®).

Figure 3A:
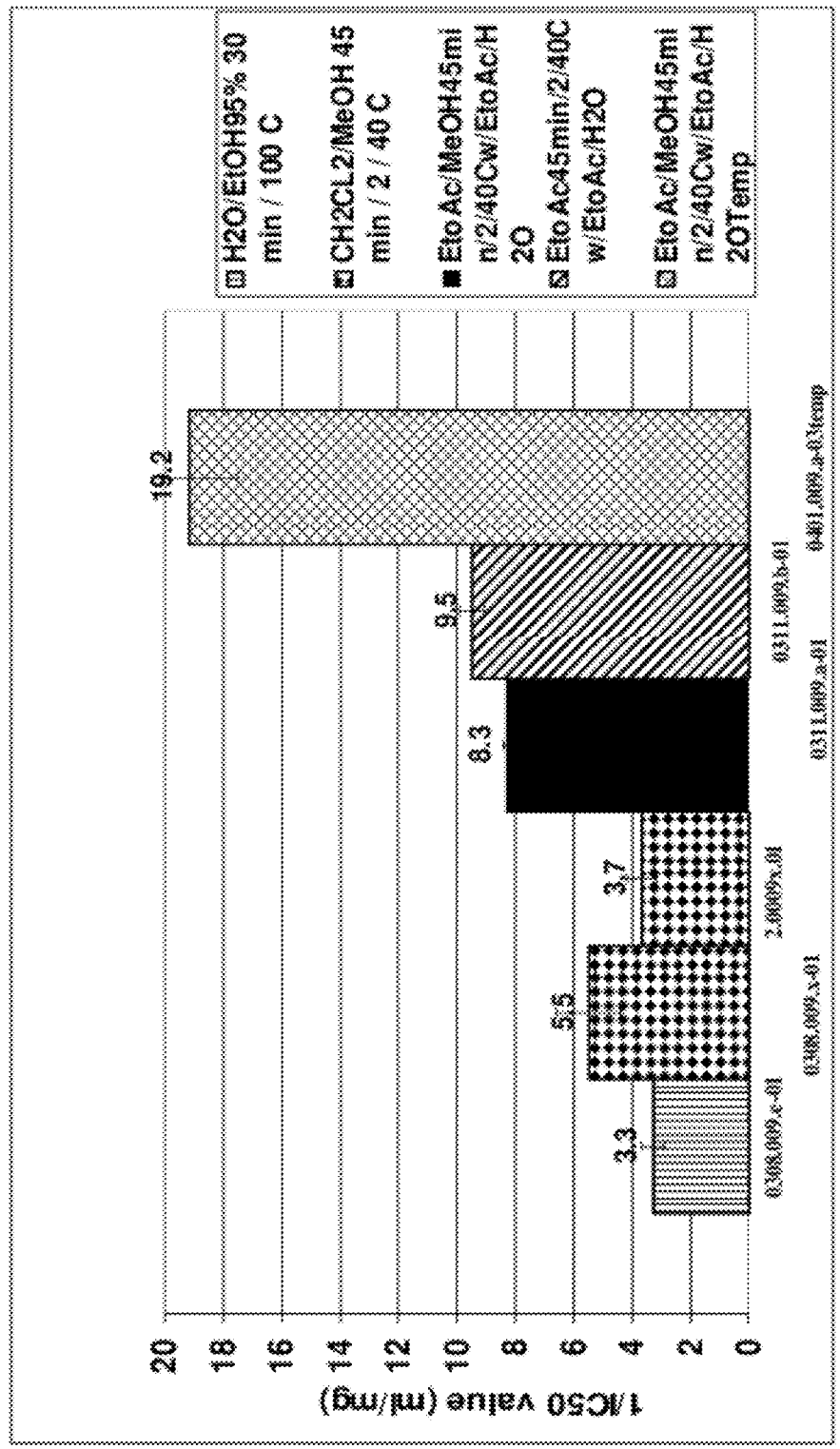
FIGS. 3A-3C provide summaries of the potencies for inhibition of cell proliferation by the different botanicals *Ganoderma lucidum* (#8), *Scutellaria barbata* (#15), and *Salvia miltiorrhiza* (#14).
Figure 3B:
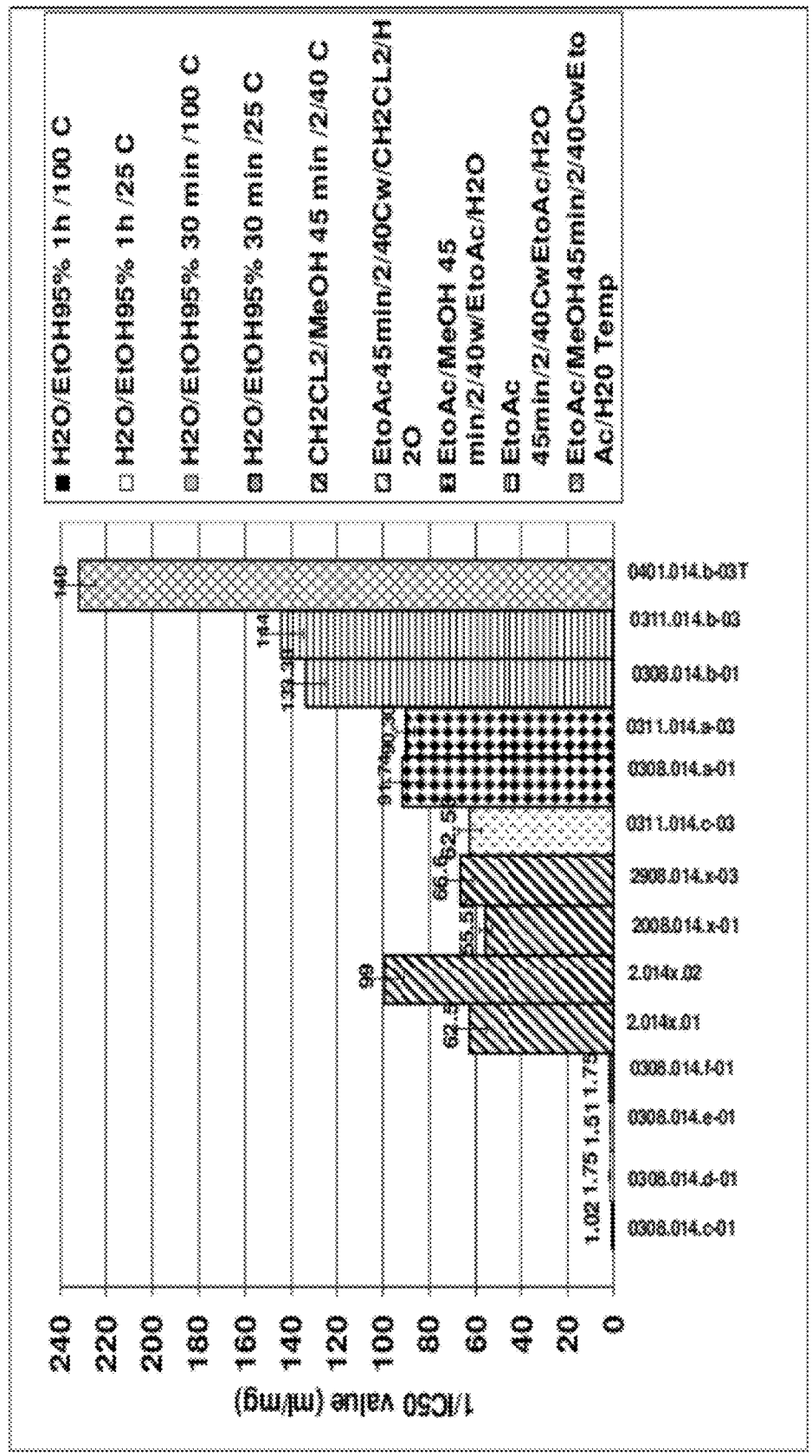
Figure 3C:
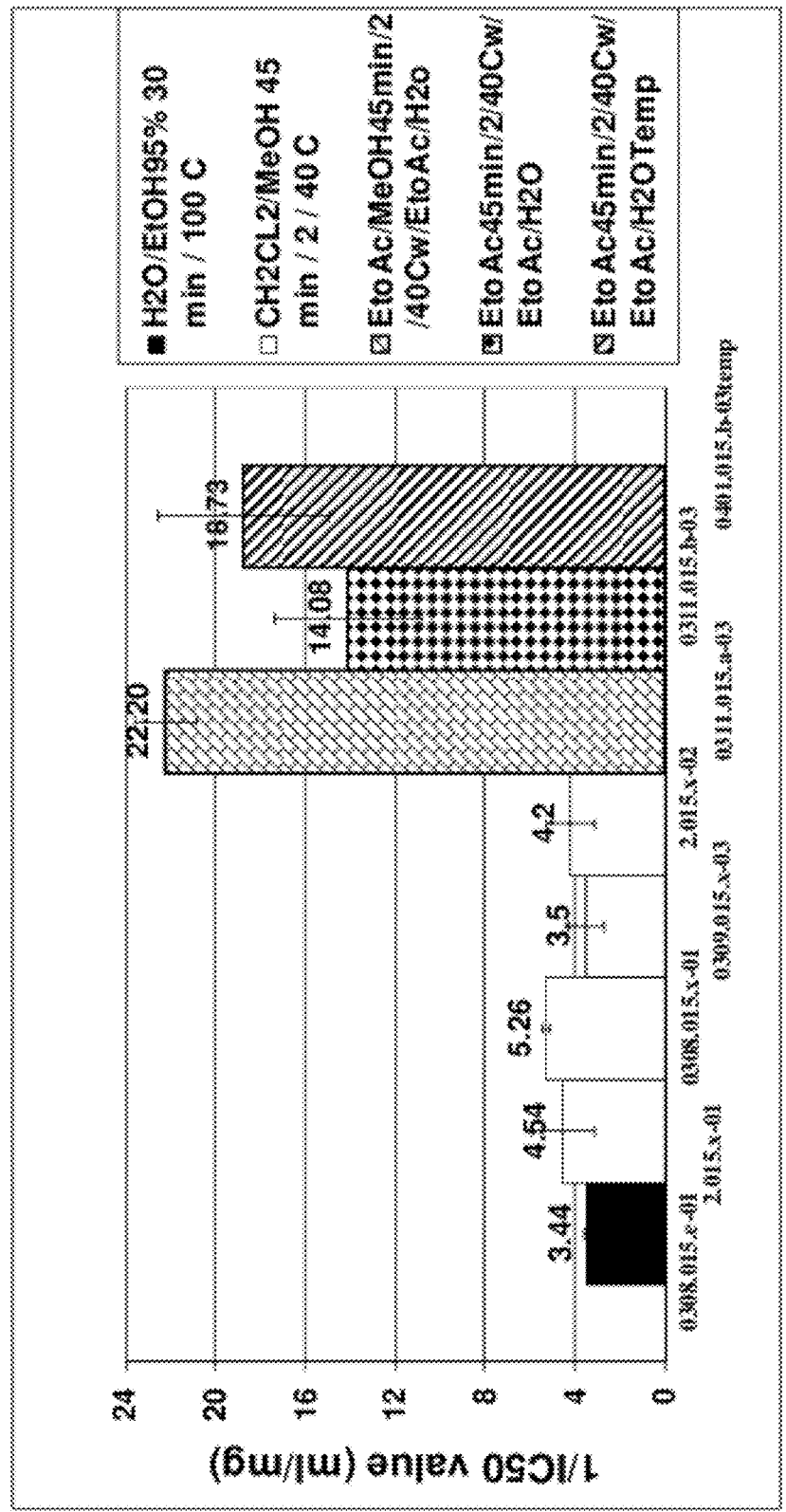

Organic and aqueous extracts were compared for efficacy. FIGS. 3A-3C provide summaries of the potencies for inhibition of cell proliferation by the different botanicals *Ganoderma lucidum* (#8), *Scutellaria barbata* (#15), and *Salvia miltiorrhiza* (#14) respectively when extracted multiple times and by different methods. Extractions by water, ethyl acetate (ester) and methanol were tested.

Example 3

Cox-2 Inhibition by Extracts

Cyclooxygenase (Cox) is an enzyme naturally present in our body. Cox-2 is an enzyme that is necessary for inducing pain. Nonsteroidal anti-inflammatory drugs (NSAIDs) are widely used in treating pain and the signs and symptoms of arthritis because of their analgesic and anti-inflammatory activity. It is accepted that common NSAIDs work by blocking the activity of cyclooxygenase (COX), also known as prostaglandin G/H synthase (PGHS), the enzyme that converts arachidonic acid into prostanoids. Recently, two forms of COX were identified, a constitutive isoform (COX-1) and an inducible isoform (COX-2) of which expression is upregulated at sites of inflammation (Vane, J. R.; Mitchell, J. A.; Appleton, I.; Tomlinson, A.; Bishop-Bailey, D.; Croxtoll, J.; Willoughby, D. A. Proc. Natnl. Acad. Sci. USA, 1994, 91, 2046). COX-1 is thought to play a physiological role and to be responsible for gastrointestinal and renal protection. On the other hand, COX-2 appears to play a pathological role and to be the predominant isoform present in inflammation conditions. The Cox2 enzyme is specific for inflammation, and Cox2 inhibitors (such as CELEBREX® (Celecoxib), VIOXX® (Rofecoxib)) were recently approved by the FDA.

A large body of evidence suggests that cyclooxygenase-2 (COX-2) is important in gastrointestinal cancer. Levels of COX-2 mRNA were increased by >60-fold in pancreatic cancer compared to adjacent nontumorous tissue. (Tucker et al., Cancer Res. 1999 Mar. 1; 59(5):987-990.) Cyclooxygenase-2 (COX-2) was overexpressed in squamous cell carcinoma of the head and neck (HNSCC) but was undetectable in normal oral mucosa from healthy subjects. (Chan et al., Cancer Res. 1999 Mar. 1; 59(5):991-994). There is now increasing evidence that a constitutive expression of COX-2 plays a role in development and progression of malignant epithelial tumors. (Denkert et al Cancer Res. 2001 Jan. 1; 61(1):303-308.) Taken together, these results suggest that COX-2 may be a target for the prevention or treatment of cancer.

The anti-inflammatory assays for COX-2 inhibitory activity were conducted using prostaglandin endoperoxide H synthase-1 and -2 isozymes (PGHS-1, and -2) based on their ability to convert arachidonic acid to prostaglandins (PGs). The positive controls used in this experiment are aspirin, naproxen, and ibuprofen.

Figure 4:
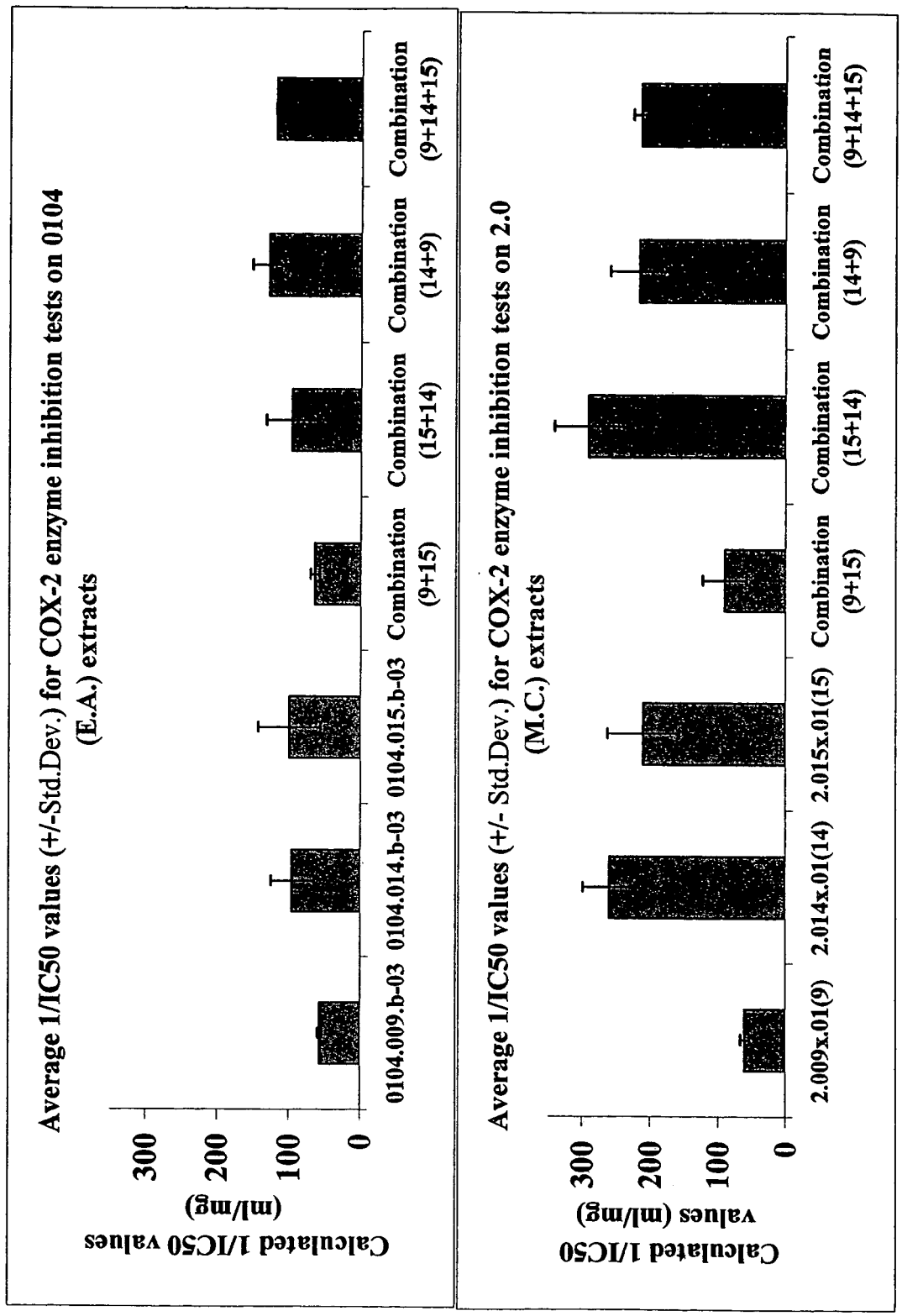
FIG. 4 shows combination index (CI) values for the inhibition of COX-2 enzyme activity by ethyl acetate (upper panel) and methylene chloride (lower panel) extracts of the individual botanicals *Ganoderma lucidum* (#8), *Scutellaria barbata* (#15), and *Salvia miltiorrhiza* (#14) and combinations thereof.

Combination index (CI) values for the inhibition of COX-2 enzyme activity by methylene chloride extracts of the individual botanicals *Ganoderma lucidum* (#9), *Scutellaria barbata* (#15), and *Salvia miltiorrhiza* (#14) and combinations thereof were measured. The inverse of the concentration of extract(s) that inhibited enzyme activity by 50% of maximum inhibition (as measured by heat inactivation) is shown in FIG. 4. The combination of *Ganoderma lucidum* (#9) and *Salvia miltiorrhiza* (#14) showed the most synergism as did the Aneustat combination of all three botanicals.

Figure 5:
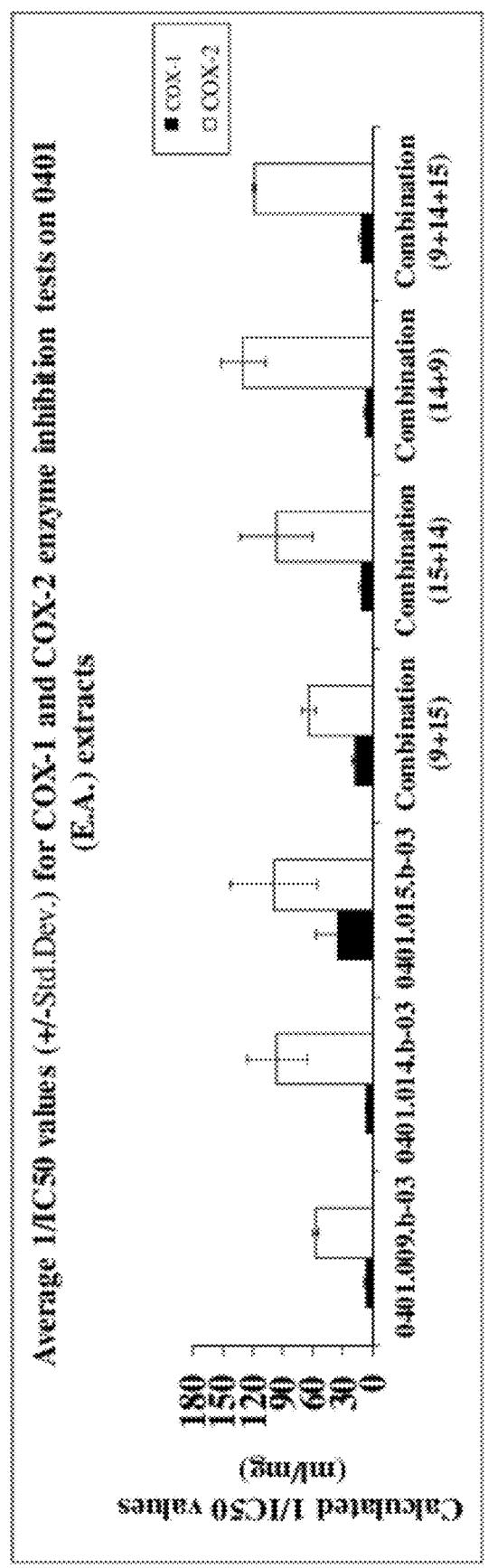
FIG. 5 shows combination index (CI) values for the inhibition of COX-1 and COX-2 enzyme activities by ethyl acetate extracts of the individual botanicals *Ganoderma lucidum* (#8), *Scutellaria barbata* (#15), and *Salvia miltiorrhiza* (#14) and combinations thereof.

Combination index (CI) values for the inhibition of COX-2 enzyme activity by ethyl acetate extracts of the individual botanicals *Ganoderma lucidum* (#8), *Scutellaria barbata* (#15), and *Salvia miltiorrhiza* (#14) and combinations thereof were measured. The inverse of the concentration of extract(s) that inhibited enzyme activity by 50% of maximum inhibition (as measured by heat inactivation) is shown in FIG. 5. The combination of *Ganoderma lucidum* (#9) and *Scutellaria barbata* (#15) showed any significant synergism (CI ~0.6).

Figure 6:
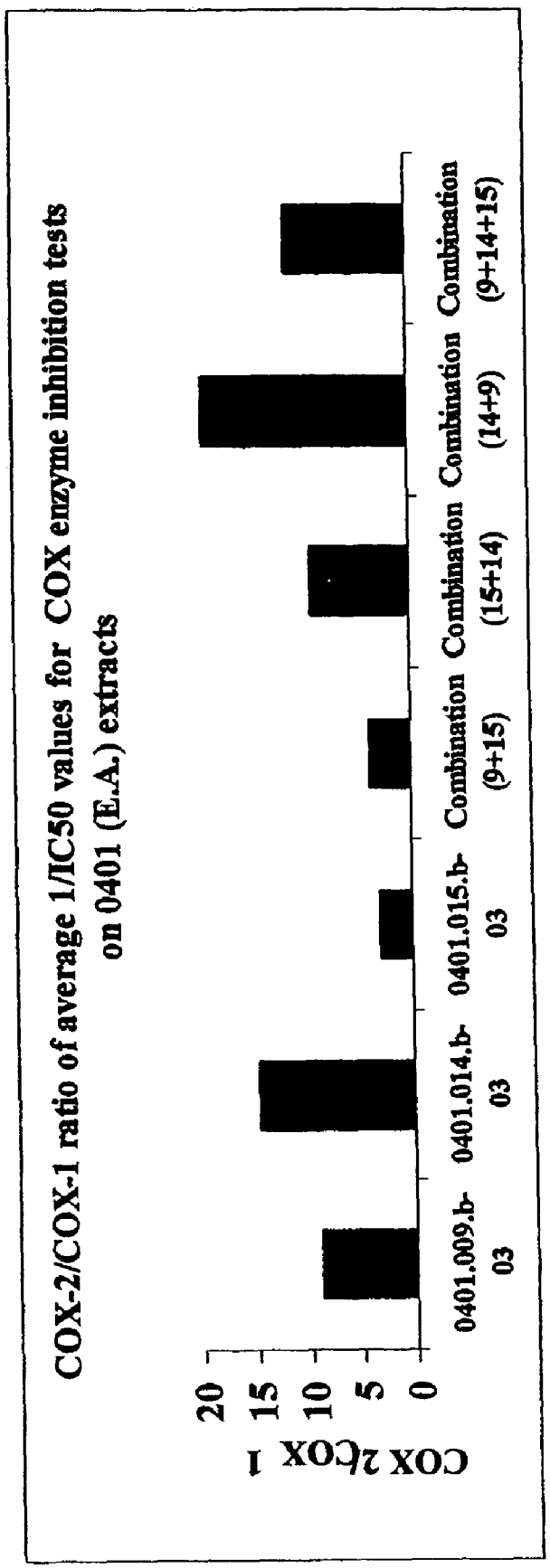
FIG. 6 shows the ratio of the potencies of inhibition of COX-2 over inhibition of COX-1 by ethyl acetate extracts (#0401) of the individual botanicals *Ganoderma lucidum* (#8), *Scutellaria barbata* (#15), and *Salvia miltiorrhiza* (#14) and combinations thereof.

A preferred COX-2 inhibitor would exhibit greater inhibition of COX-2 over COX-1, which is responsible for gastrointestinal and renal protection. The ratio of the potencies of inhibition of COX-2 over inhibition of COX-1 by ethyl acetate extracts (#0401) of the individual botanicals *Ganoderma lucidum* (#8), *Scutellaria barbata* (#15), and *Salvia miltiorrhiza* (#14) and combinations thereof were measured and is shown in FIG. 6. The combinations shown were prepared by mixing two or more extracts in the ratios of their IC50s for inhibiting either COX-1 or COX-2 activity. Thus different combination mixtures were used for COX-1 and COX-2 inhibition. The extract of *Salvia miltiorrhiza* (#14) was the most selective single agent and showed a 15-fold preference for COX-2 over COX-1. The combination of extracts of *Ganoderma lucidum* (#9) and *Salvia miltiorrhiza* (#14) was 19-fold more potent in inhibiting COX-2 over COX-1 a shown in FIG. 6.

Figure 7:
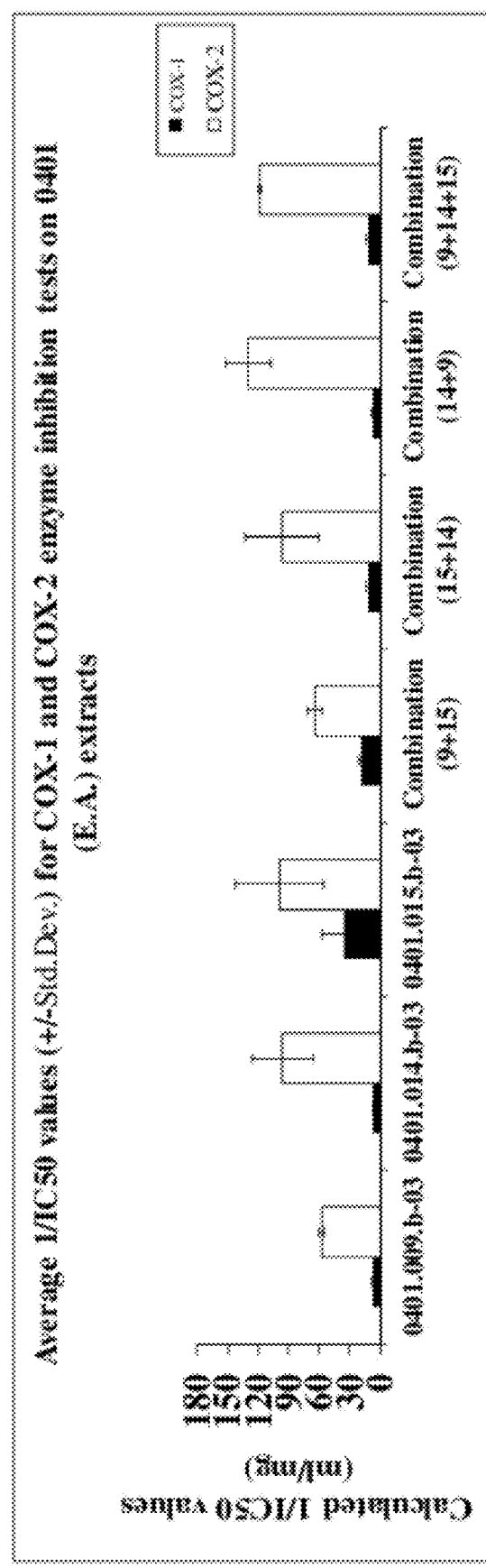
FIG. 7 shows the potencies for inhibition of COX-2 and COX-1 by ethyl acetate extracts (#0401) of the individual botanicals *Ganoderma lucidum* (#8), *Scutellaria barbata* (#15), and *Salvia miltiorrhiza* (#14) and combinations thereof.

FIG. 7 shows the potencies for inhibition of COX-2 and COX-1 by ethyl acetate extracts (#0401) of the individual botanicals *Ganoderma lucidum* (#8), *Scutellaria barbata* (#15), and *Salvia miltiorrhiza* (#14) and combinations thereof. Potency is represented as the inverse of the $IC_{50}$ of each composition tested. Inhibition was measured by COX-1 and COX-2 ELISA assay kits (Cayman Chemical Co., Ann Arbor, Mich.). *Salvia miltiorrhiza* (#14) alone or in combination with *Ganoderma lucidum* (#9), or *Ganoderma lucidum* (#9) and *Scutellaria barbata* (#15) showed the most potency.

Example 4

Anti-Oxidant Activity of Extracts

Blends of botanical extracts comprising two or more of sea buckthorn berry, sea buckthorn leaf, Pq (*Panax quinquefolium*), *Ganoderma lucidum, Salvia miltiorrhiza*, and *Scutellaria barbata* are tested for anti-oxidant property. Blend A comprised all 6 ingredients and Blends B-G specifically excluded one component at a time. Sea buckthorn leaf was found to be responsible for nearly 50% of the anti-oxidant activity of the entire blend.

Blends of hot water extracts comprising two or more of *Ganoderma lucidum, Salvia miltiorrhiza*, and *Scutellaria barbata* are tested for anti-oxidant property expressed. The standard of comparison is Trolox (a water-soluble analog of vitamin E), and the relative anti-oxidant activity is defined as Trolox Equivalents (TE). The standard of comparison in is Quercetin (a flavonoid), and the relative anti-oxidant activity is defined as Quercetin Equivalents. Sea buckthorn leaf was found to be responsible for nearly 50% on the anti-oxidant activity of the entire blend under both systems of measurement.

Example 5

TNF-α Assay of Extracts

Tumor burden results in significant increases in circulating tumor necrosis factor-α (TNF-α), a cytokine which can induce protein breakdown in skeletal muscle. (Llover et al., Mol Cell Endocrinol. 1998 Jul. 25; 142(1-2):183-189). TNF-α is a cytotoxic cytokine released from stimulated lymphocytes. TNF-α targets tumor cells that are undergoing aberrant mitosis On reaching a target cell, TNF-α binds to a receptor and causes the cell to undergo apoptosis. TNF-α is releases from a number of lymphocytes including macrophages, neutrophils, activated T and B lymphocytes, neatural killer cells, etc. TNF-α is also a primary regulator of the immune response.

Figure 8:
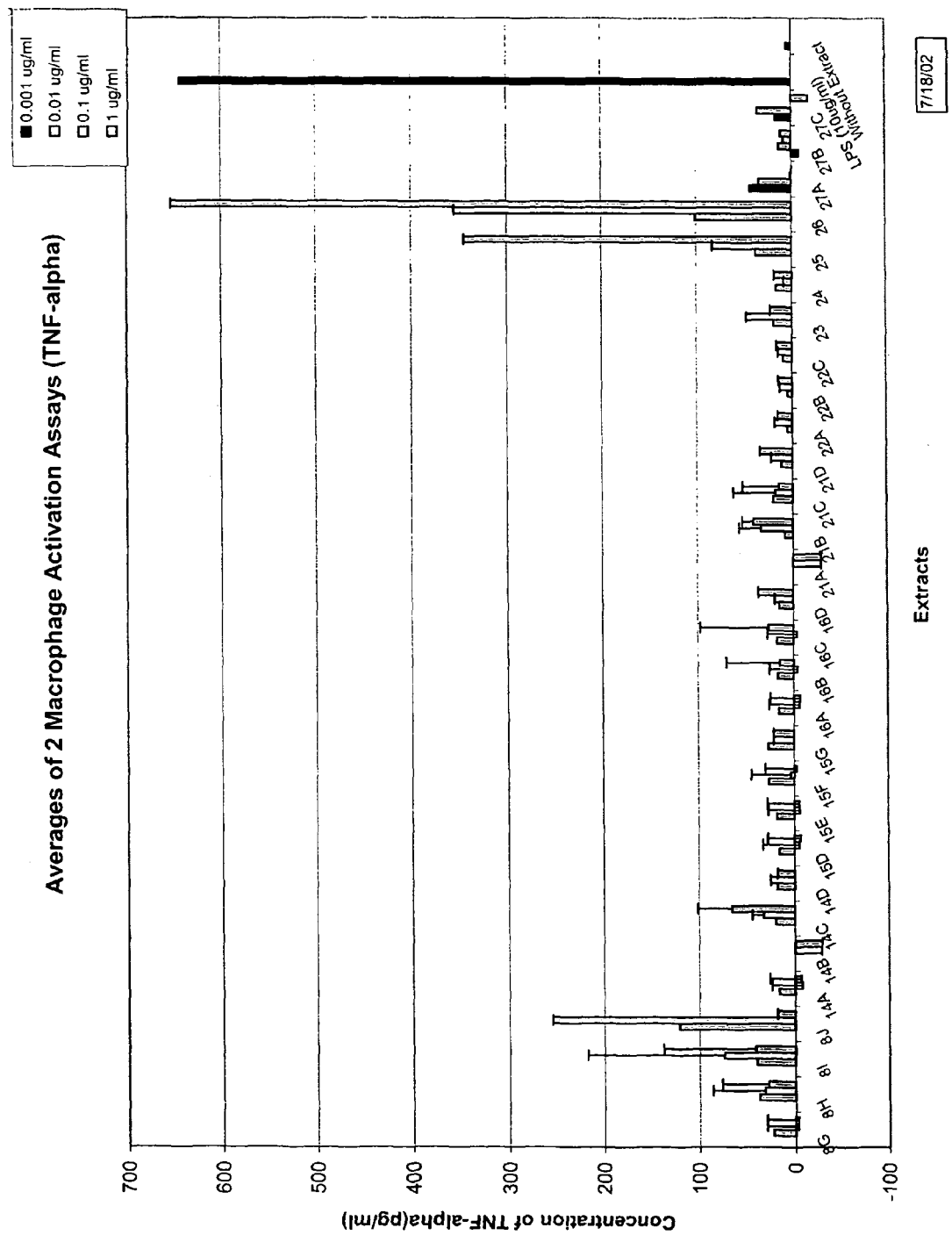
FIG. 8 shows monocytes (macrophage precursors) treated with different concentrations of extracts of *Ganoderma lucidum* (#8), *Scutellaria barbata* (#15), and *Salvia miltiorrhiza* (#14) and the release of TNF-α (tumor necrosis factor-alpha) measured by an ELISA immunoassay.

The extracts were tested for the ability to stimulate macrophages to release TNF-α. Monocytes (macrophage precursors) were treated with different concentrations of extracts of one or more of *Ganoderma lucidum* (#8), *Scutellaria barbata* (#15), and *Salvia miltiorrhiza* (#14) for 4 hours and the release of TNF-α is measured by an ELISA immunoassay. The results are shown in FIG. 8. *Ganoderma lucidum* displays the most potent ability to induce TNF-α release.

Example 6

Ability of Extracts to Enhance Immune System Activity

Figure 9:
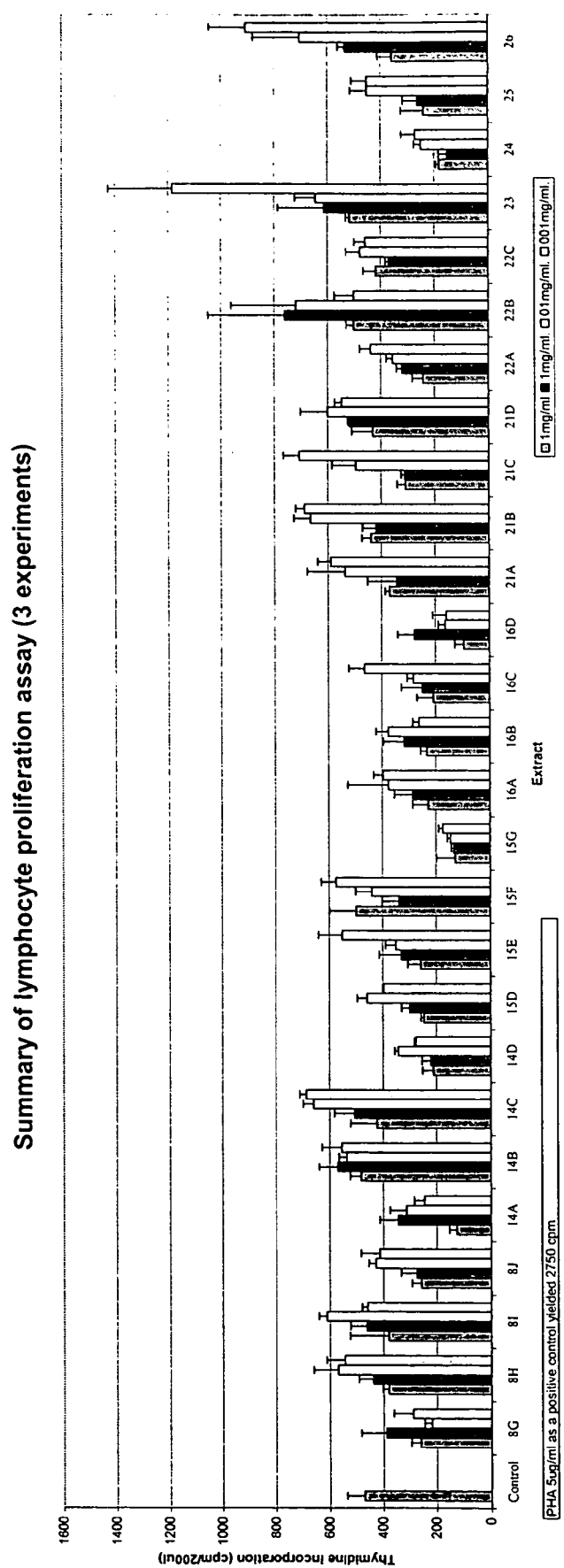
FIG. 9 shows lymphocyte proliferation induced by *Ganoderma lucidum* (#8), *Scutellaria barbata* (#15), and *Salvia miltiorrhiza* (#14).

The proliferation of lymphocytes is related to the enhancement of the immune system as it represents the availability of larger number of cells of the immune system that become available to encounter pathogens. Different concentrations of extracts of *Ganoderma lucidum* (#8), *Scutellaria barbata* (#15), and *Salvia miltiorrhiza* (#14) were tested for the ability to enhance proliferation of cells of the immune system. The proliferation of lymphocytes was measured as the amount of tritiated thymidine incorporated into the DNA of lymphocytes and is shown in FIG. 9.

Example 7

Ames Test for Measurement of Mutagenicity of Extracts

The use of the Ames test is based on the assumption that in addition to causing tumors in animal cells, most carcinogens are mutagens. The bacterium used in the test is a strain of *Salmonella typhimurium* that caries a mutation in the his operon making it unable to synthesize the amino acid histidine (His) from the ingredients in its culture medium. with mutations in the his operon are histidine auxotrophs—they are unable to grow without added histidine. Revertants that restore the His$^+$ phenotype will grow on minimal medium plates without histidine. This provides a simple, sensitive selection for revertants of his mutants as mutagens. (Ames, B., F. Lee, and W. Durston. 1973. An improved bacterial test system for the detection and classification of mutagens and carcinogens. Proc. Natl. Acad. Sci. USA 70: 782-786).

Figure 10:
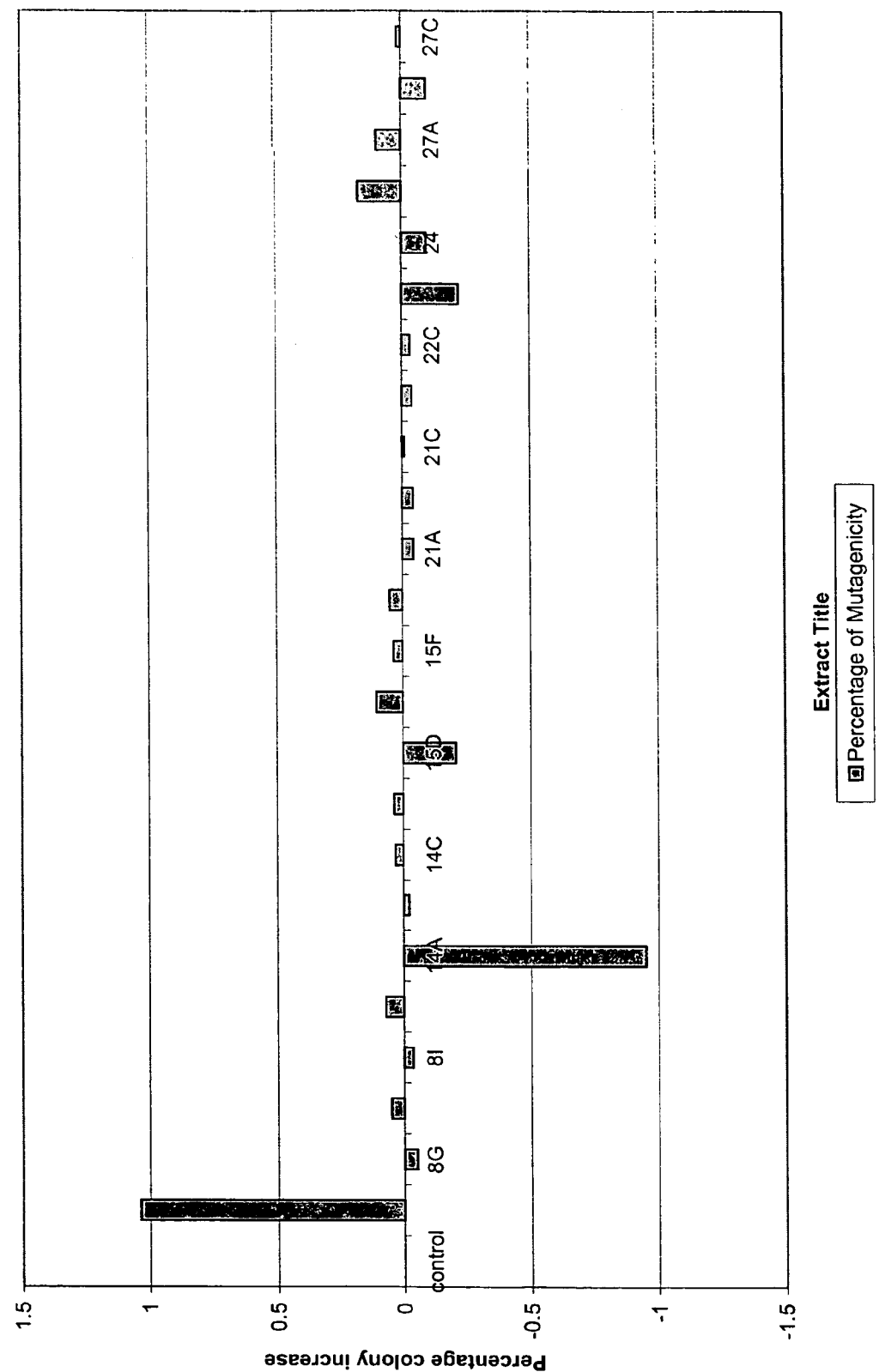
FIG. 10 shows Ames test performed on extracts of *Ganoderma lucidum* (#8), *Scutellaria barbata* (#15), and *Salvia miltiorrhiza* (#14) at 20 µg per plate.

The Ames test shows whether the compositions tested are themselves mutagenic and thus potentially dangerous. The test could also show whether the extracts are beneficial by preventing mutations. Many compounds were altered in the liver to become mutagenic. The tests were thus performed in the presence and absence of liver enzymes (liver extract activated with NADPH and glucose-6-phosphate). 2-aminoantracene was used as positive control. The Ames test was performed on extracts of *Ganoderma lucidum* (#8), *Scutellaria barbata* (#15), and *Salvia miltiorrhiza* (#14) at 20 µg per plate and are shown in FIG. 10. None of the extracts showed any significant mutagenicity.

Example 8

Maximum Tolerable Dose of ANEUSTAT™

Figure 11:
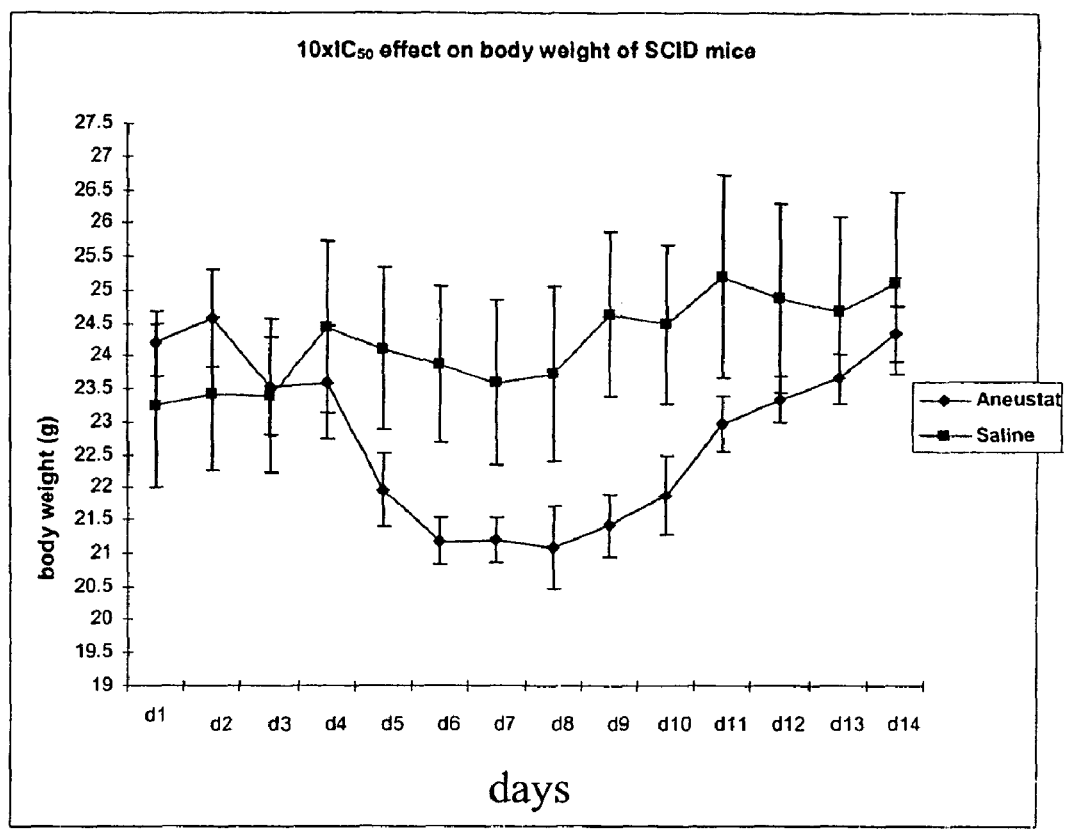
FIG. 11 shows the effects of Aneustat on the body weight of SCID (severe combined immunodeficiency) mice.

A solution of ANEUSTAT™ *Ganoderma lucidum*, *Salvia miltiorrhiza*, and *Scutellaria barbata*) representing 10× IC50 was administered orally to SCID/nod mice. A solution of the extracted material (43.65 mg/ml.) was administered orally (1 ml/day/animal) to SCID/nod mice (25 gm; n=5) once a day for up to 14 days. The mice were monitored over a 28-day period for signs of stress following drug administration, including substantial loss of body weight, diarrhea, heavy panting, ruffling of hair, etc. On days 2 through 14, less than 13% body weight loss was observed (FIG. 11) and the animals were considered to be healthy. At the end of the period mice were terminated by CO2 inhalation. Age-matched control mice (n=4) were treated with saline 1 ml/day for the 14 days. The data show that a daily dosage of 43.65 mg/ml/25 gm mouse of the extract is not toxic. This dosage was used in a preliminary study on the effect of the extract on tumor growth in a xenograft model system.

Example 9

Establishment of a Human Lung Cancer Tissue Xenograft/Mouse Model

Pre-clinical testing of lung cancer therapeutics has been largely carried out using xenograft models in which human lung cancer cell lines have been subcutaneously injected into immunodeficient mice. However, cancer cell xenografts may not accurately mimic the behavior of lung tumors in vivo. In fact, cancer cell line xenograft models have a poor record of accurately predicting the clinical efficacy of anticancer agents. A novel xenograft model was established for a variety of pre-cancerous and cancerous human tissues, including lung cancer tissue. Most importantly, the xenografts in the model retain the histological characteristics of the parental tissue. For selected types of cancer that the xenografts respond to therapy in a manner similar to that observed in patients. For example, prostate cancer tissue grown in SCID mice showed a dramatic response to androgen ablation therapy as regularly found in the clinic.

After two and half months of growth of a AB79 lung cancer xenograft in vivo, one of two tissue xenografts had grown to the size of a walnut. Tumors grafted to the renal site survived and retained their original histopathology and differentiation marker profile, even after serial passaging. The lung cancer tissue has a very rapid growth rate in SCID mice with a doubling time about 5 days. Cytogenetic analyses did show some abnormal chromosomes. Not only are there translocations, there are also deletions and duplication of chromosomal segments. (note: since each chromosome has it's own display color, more than one color along the length of a chromosome indicates a translocation). The Spectral Karyotyping (SKY) analysis showed that the tissue of a AB79 lung cancer xenograft contained only a low number of karyotypic alterations, although the cancer was highly advanced.

Example 10

Figure 12:
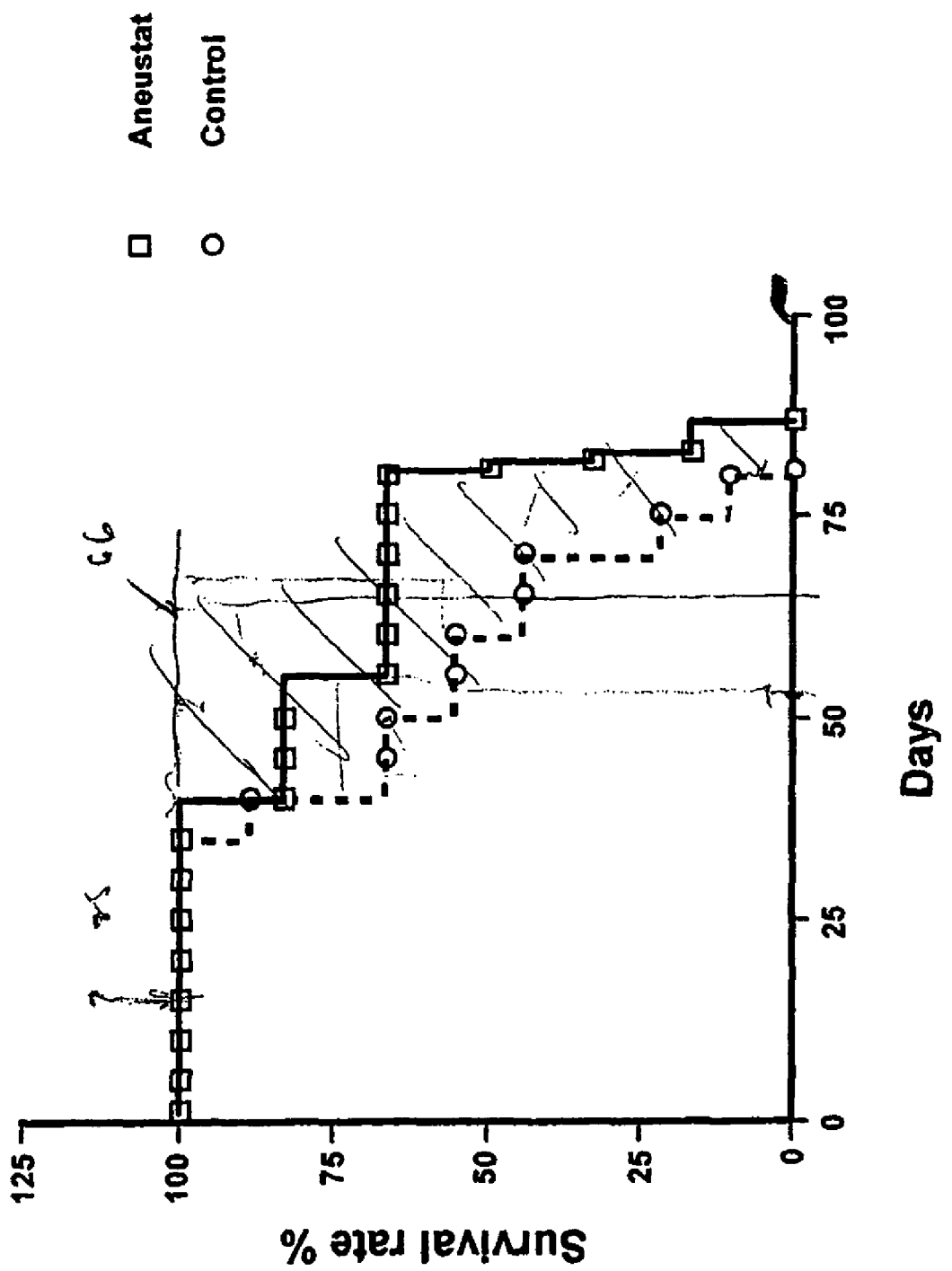
FIG. 12 shows survival curve for A549 cell line treated with Aneustat.

Survival Effect of Aneustat on Mice Carrying Human Lung Cancer Cell Line A549 Xenografts Human A549 cells were mixed with collagen gel ($10^6$ cells/gel) and grafted under the renal capsules of 3 SCID/nod mice. After 2 months in vivo, A549 cells had formed solid tumors which were then harvested and dissected into multiple identical pieces. Four pieces (each piece about 2.5 mm$^3$) of tumor were grafted into one mouse on day 0. In total 60 pieces were grafted into 15 mice. 25 days after grafting the average tumor volume was 20.8 mm$^3$. Aneustat was the administered orally (14.4 mg/animal/day) to 6 mice for 21 days. Age-matched control mice were treated with saline fr the same period. the results of the survival of the mice were monitored over a 12-week period and shown in FIG. 12. A 3 week treatment with Aneustat imparted significant increase in survival of A549 tumor bearing mice over a 3 month period.

Example 11

Effect of Aneustat on Growth of Human, Drug Resistant, Small Cell Lung Cancer (AB79) Xenografts The efficacy of of Aneustat against drug resistant small cell lung carcinoma (SCLC) was tested using xenografts from a 68 year old patient with drug-resistant SCLC. 80 tumor tissue pieces (2 mm$^3$) were randomly grafted into 24 mice under the renal capsule on day 0. At the start of the treatment (day 6), the average tumor volume was about 5 mm$^3$, increasing to 600 mm$^3$ on day 21 in the control group.

On day 7, when the average graft volume was about 5 mm$^3$, ANEUSTAT™ treatment was initiated. 3 groups of 6 mice each were treated with 43.65, 14.4 and 4.3 mg/animal/day respectively for 16 days after which the grafts were harvested to determine the effect on tumor volume, histology, apoptosis index (Tunel assay) and proliferation index (proliferation marker Ki67 staining). TUNEL assay detects apoptosis-induced DNA fragmentation through a quantitative fluorescence assay. Terminal deoxynucleotidyl transferase (TdT) catalyzes the incorporation of bromo-deoxyuridine (BrdU) residues into the fragmenting nuclear DNA at the 3'-hydroxyl ends by nicked end labeling. A TRITC (Tetramethyl Rhodamine Iso-Thiocyanate)-conjugated anti-BrdU (Bromodeoxyuridine) antibody can then label the 3'-hydroxyl ends for detection.

Figure 13:
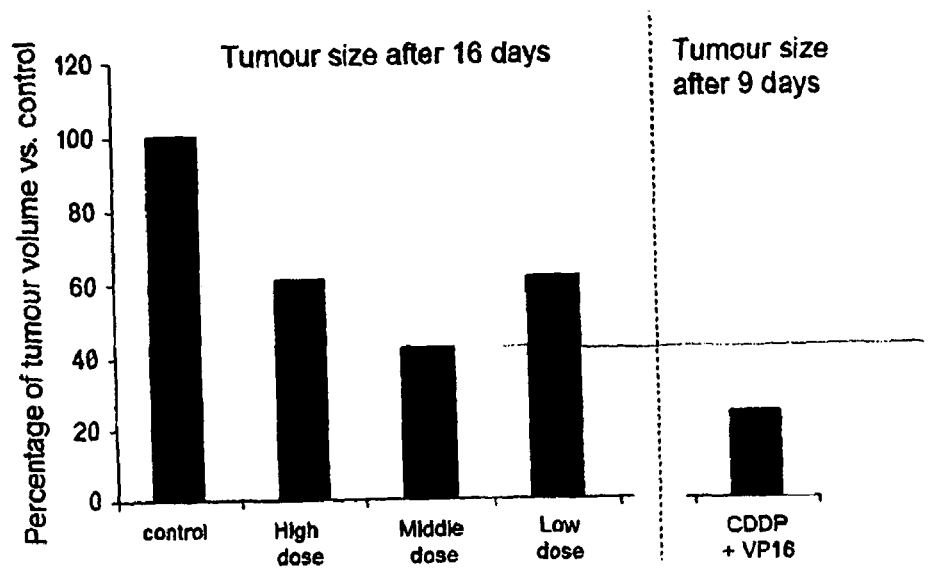
FIG. 13 shows effects of Aneustat treatment on the growth of SCLC (small cell lung cancer) xenografts.

ANEUSTAT™ treatment inhibited SCLC xenograft growth substantially in all three doses (by >50% at a dosage of 14.4 mg/mouse/day) in a statistically significant manner ($p<0.01$). The mixed botanical extract inhibited the growth of the lung cancer tissue substantially at all 3 dosages, by about 50%. The differences between tumor growth in control and treated animals were statistically significant ($p<0.01$). The inhibitory effect was comaparable to standard chemotherapeutic regimen of CDDP (cis-diamminedichloroplatinum (II); cisplatin)+VP16 (etoposide) and is shown in FIG. 13.

Figure 14:
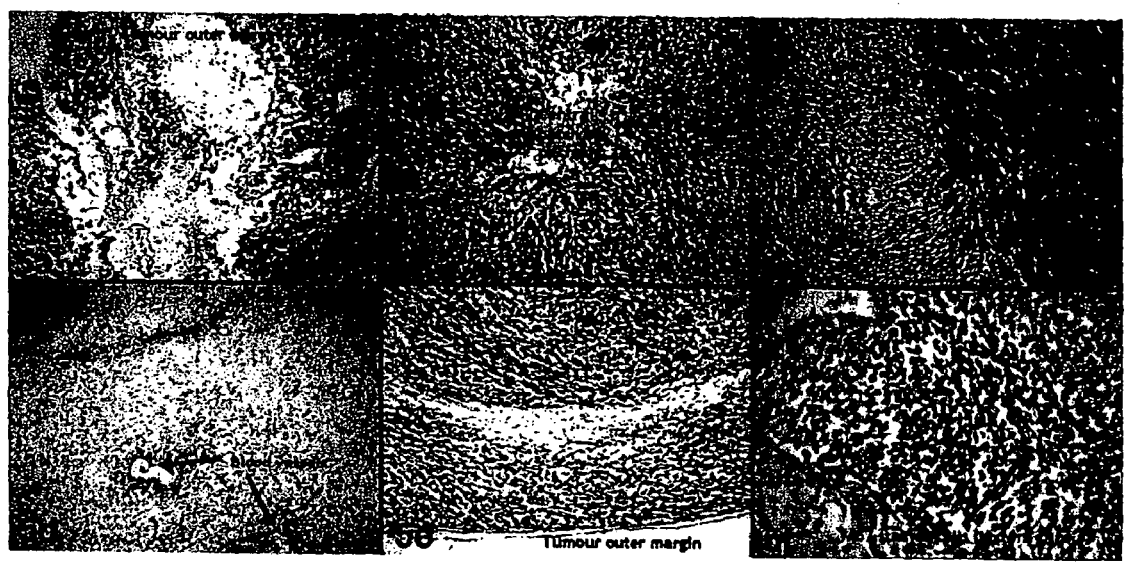
FIG. 14 shows effects of Aneustat treatment on SCLC xenograft histopathology.

Histopathology showed differences in necrotic patterns. In untreated xenografts, necrosis was principally focal and central as is common in all small cell anaplastic carcinoma and reflects vaso-distal necrosis caused by rapid proliferation (FIG. 14a). The necrotic cells were predominantly located in the central portions of the tumor (FIG. 14b). The Ki67 immunostaining showed usual increases in proliferation adjacent to areas of necrosis without signs of repair (FIG. 14c).

In ANEUSTAT™ treated xenografts, necrosis was increased and was principally confluent rather than focal. Necrosis was vasocentric (FIG. 14d) and was present in juxtaposition to the advancing tumor margin rather than centrally (FIG. 14e). Ki67 immunostains showed overall increase in the number of cells in "S" phase and this was particularly marked at the advancing edge (FIG. 14f). Increased blood supply and blood-delivered cytotoxicity in the region of active growth may be inferred from these observations. Increase in S phase cells and increase in proliferative activity may indicate a "protective" effect of the ANEUSTAT™ composition. The hesalthy appearance of ANEUSTAT™-treated xenografts (in comparison with the appearance of CDDP+VP16 treated xenografts) may reflect cytostatic effects or the reduced toxicity of the composition.

Apoptosis was measured using a APOPTAG® Fluorescein In Situ Apoptosis Detection Kit (Chemicon). Significantly more cells were in apoptosis in ANEUSTAT™-treated xenografts. Programmed cell death induced by ANEUSTAT™ treatment is an important property as cancers often proliferate by neutralizing a cell's ability to apoptose.

Figure 15:
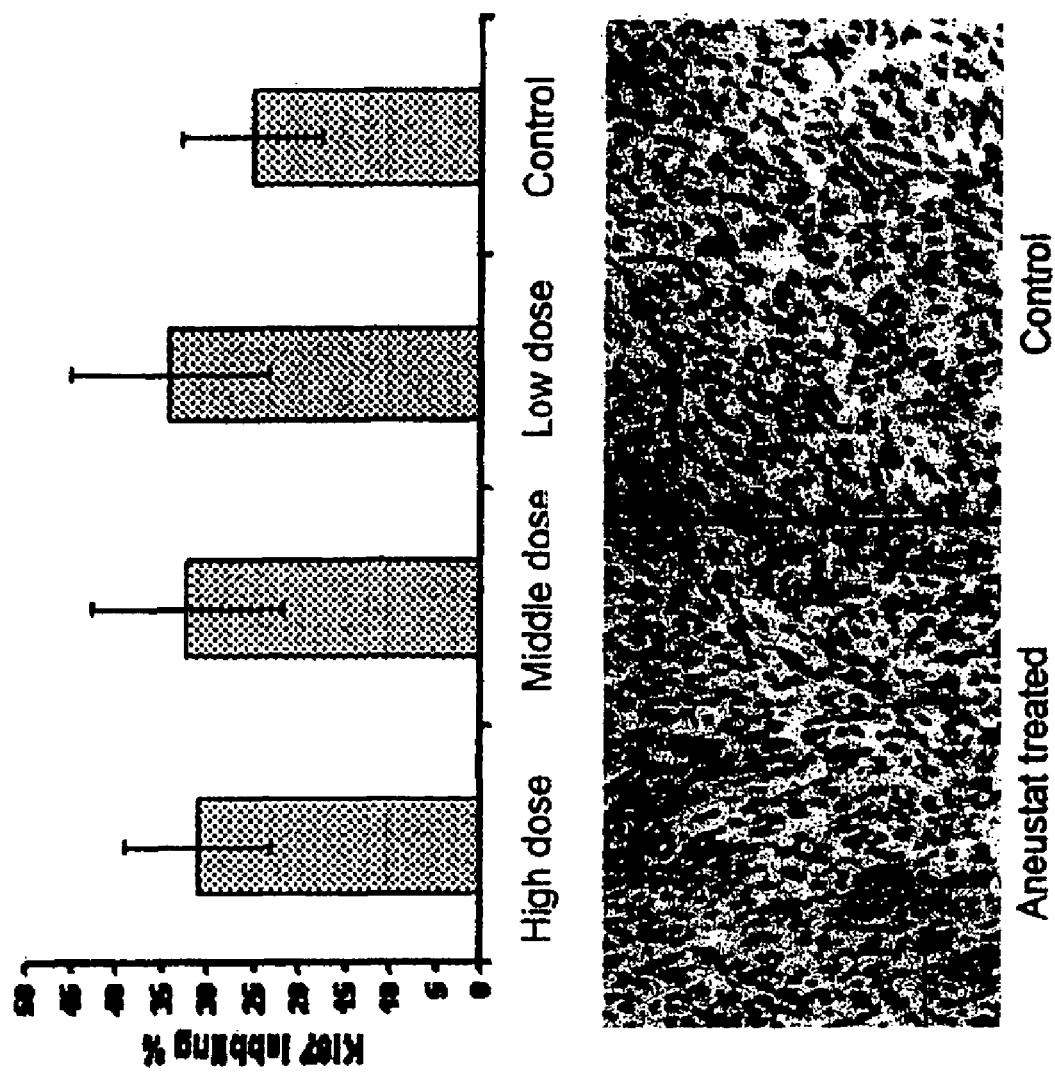
FIG. 15 shows effects of Aneustat treatment on SCLC cell proliferation.

Grafts stained with anti-Ki67 antibody showed a marginal, but statistically significant, increase in Ki67 staining of cancer cells after Aneustat treatment. Ki67 labels cells found in S phase indicating arrest in S phase (FIG. 15).

Example 12

Xenograft Efficacy Study on Prostate Cancer Cell Line (DU145)

Figure 16:
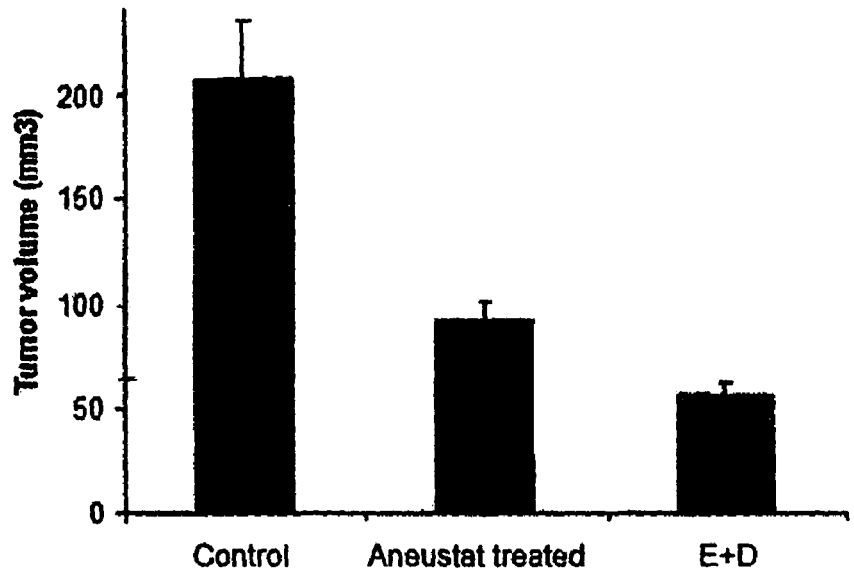
FIG. 16 shows effects of Aneustat treatment on DU145 prostate cancer cell line xenografts in vivo.

To determine the efficacy of Aneustat on other cancer types and compare its performance to a standard chemotheray regimen, tumor xenografts from a prostate cell line DU145 were cut into 2 mm$^3$ pieces and grafted into SCOD/rod mice. Treatment was started at day 13 (mean volume=15.6 mm$^3$). The mice were divided into 3 equal groups for treatment with saline, Aneustat at 3.3 IC50 and estramustine sodium phosphate (EMCYT®) and docetaxel (E+D). As shown in FIG. 16, Aneustat showed a significant inhibitory effect comparable to the E+D regimen.

Example 13

Effect of Aneustat on Growth of Non-Small Cell Lung Cancer (NSCLC) Line (AB117) Xenografts AB117 tumor showing features of lung squamous cell carcinoma was obtained from a 53 year old man with late stage disease. The xenografts were treated with saline (control), Aneustat, cisplatin+docetaxol and cisplatin+vinorelbin. Only Aneustat was administered orally, the other drugs were administered intraperitonially.

Figure 17:
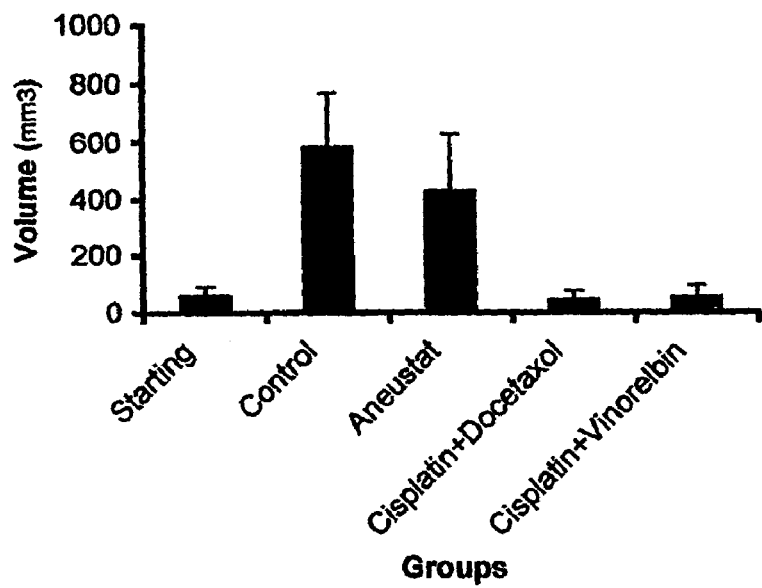
FIG. 17 shows effects of Aneustat treatment on growth of (non-small cell lung cancer) NSCLC xenografts.

As shown in FIG. 17, Aneustat has a significant inhibitory effect on the growth of human NSCLC tissue in vivo.

Figure 18:
FIG. 18 shows effects of Aneustat and cisplatin+docetaxol treatment on AB 117 NSCLC xenograft histopathology.

As shown in FIG. 18, Aneustat-treated tumors show increased pleiomorphism (18c) and multinucleated cells (18d). In contrast, control tumors show less necrosis and pleiomorphism (18a). Cisplatin+docetaxol treated tumors (18b) show only rare viable tumor cells.

Figure 19A:
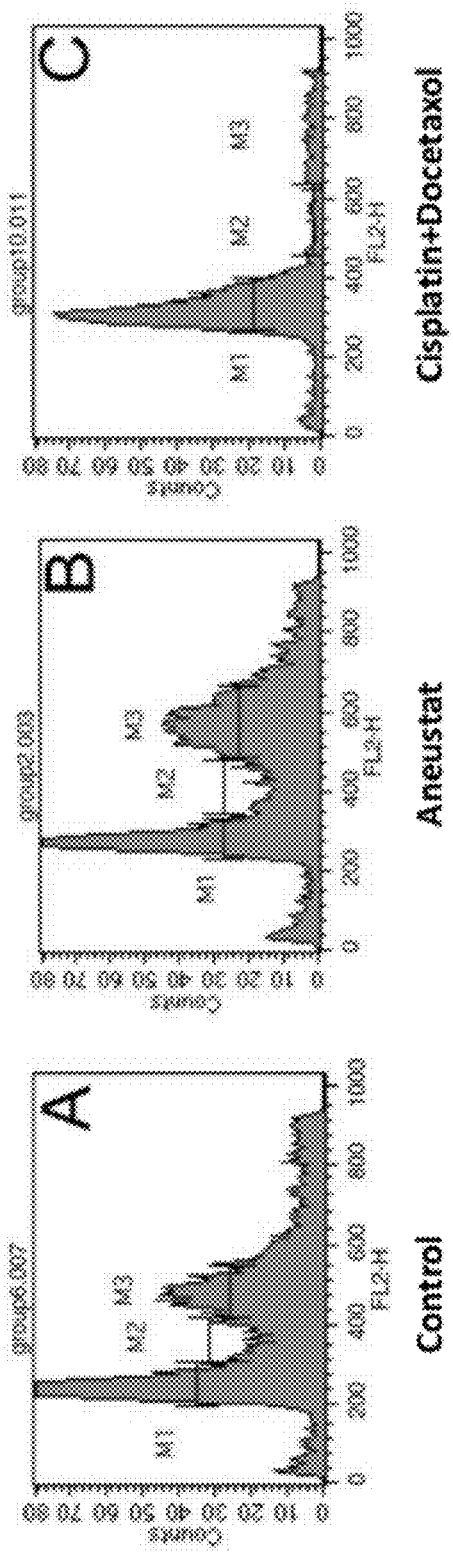
FIGS. 19A and 19B show histograms illustrating effects of Aneustat and cisplatin+docetaxol treatment on the distribution of NSCLC cells over the cell cycle.
Figure 19B:
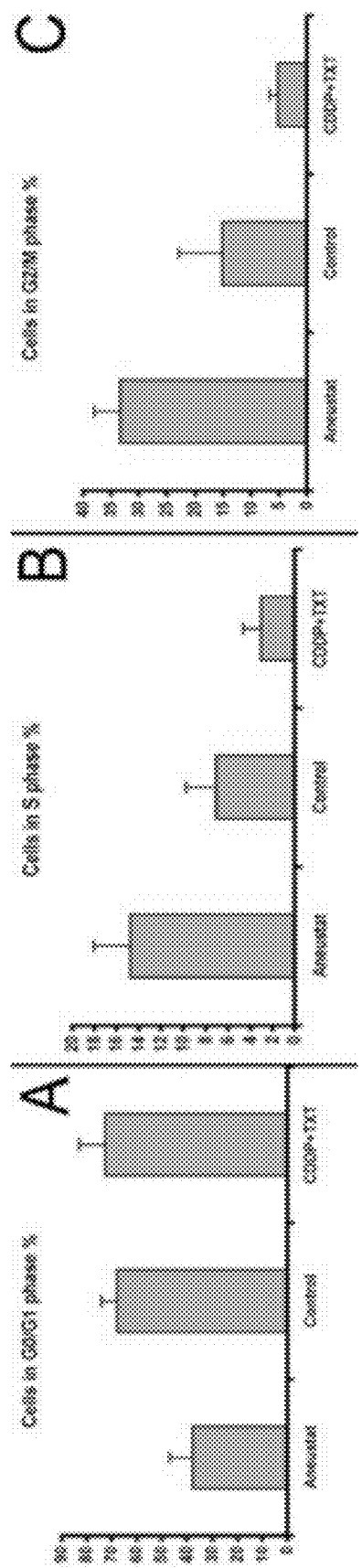

In histograms generated by fluorescence activated cell sorter (FACS) in FIGS. 19A and 19B, Cisplatin+docetaxol treated tumors show almost a total loss of cycling cells. There was some arrest in G2/M phase but cells in S+G2+M totalled only 6%. By contrast, Aneustat-treated tumors showed an increase in the percentage of S, G2 and M cells from about 30-50%. The evidence suggests that Aneustat treated cells either have a shorter G1 period or an enhanced shift from G0 to G1 reflects enhanced cycling of cells. The enhanced cycling could make the composition of Aneustat a powerful adjuvant to chemotherapy (in an Aneutox formulation) or radiation therapy.

Example 14

Anti-Proliferative Effects of Extracts on Cervical Cancer Cells

Concentrations of individual botanical extracts required for the inhibition of cervical cancer cell growth in tissue culture are tested and compared with that of ACAPHA. Organic (lipid) and aqueous (hot water) extracts are compared for efficacy. *Ganoderma lucidum, Scutellaria barbata*, Pq and *Salvia miltiorrhiza* are effective at lower concentrations than ACAPHA. Lipid fractions of the organic extracts are about 10-fold more potent than the hot water extracts.

Concentrations of lipid fractions of individual herb extracts required for 50% inhibition of cervical cancer cell growth are tested and compared with that of ACAPHA and Chinese medicine. *Salvia miltiorrhiza* is identified as the source of the most potent extract.

Concentrations of lipid fractions of combinations of herbal extracts (in mg/ml) required for 50% inhibition of cervical cancer cell growth are determined. Combinations of botanical extracts are 2 to 4-fold more potent than the most potent individual botanical extract, *Salvia miltiorrhiza*. Combinations of botanical extracts are also found to be more potent than the most effective extract of ACAPHA.

Example 15

Synergistic Inhibition of Growth of Human Cancer Cells

While extracts of *Salvia miltiorrhiza* (#14), *Ganoderma lucidum* (#9), and *Scutellaria barbata* (#15) were effective in inhibiting growth of human cancer cell lines (Tables 2A and 2B), combinations of the individual botanical extracts of *Salvia miltiorrhiza* (#14), *Ganoderma lucidum* (#9), and *Scutellaria barbata* (#15) showed synergistic effect in inhibiting human cancer cell lines from lung cancer (A549), breast cancer (MCF7), prostate cancer (DU145) and colon cancer (DLD-1) as shown in Tables 3A and 3B.

TABLE 2A $IC_{50}$ for Inhibition of Cell Proliferation by botanical extracts on different cell lines (in mg/ml with standard deviations)

| Extract | Cell Line A549 lung | | Cell Line MCF7 breast | | Cell Line DU145 prostate | | Cell Line PC-3 prostate | | Cell Line DLD-1 colon | |
|---|---|---|---|---|---|---|---|---|---|---|
| | $IC_{50}$ | Std. Dev | $IC_{50}$ | Std. Dev | $IC_{50}$ | Std. Dev | $IC_{50}$ | Std. Dev | $IC_{50}$ | Std. Dev |
| 0401.009.b-03 | 0.078 | 0.0014 | 0.112 | 0.0024 | 0.067 | 0.015 | 0.11 | 0.0028 | 0.11 | 0.025 |
| 0401.014.b-03 | 0.014 | 0.0069 | 0.0069 | 0.0035 | 0.0078 | 0.00011 | 0.014 | 0.0063 | 0.0034 | 0.00065 |
| 0401.015.b-03 | 0.073 | 0.058 | 0.062 | 0.01 | 0.049 | 0.019 | 0.068 | 0.0089 | 0.059 | 0.019 |

TABLE 2B $IC_{50}$ for Inhibition of Cell Proliferation by botanical extracts on different cell lines with standard errors of the mean

| Extract | Cell Line A549 | | Cell Line MCF7 | | Cell Line DU145 | | Cell Line PC-3 | | Cell Line DLD-1 | |
|---|---|---|---|---|---|---|---|---|---|---|
| | $IC_{50}$ | Std Err | $IC_{50}$ | Std Err | $IC_{50}$ | Std Err | $IC_{50}$ | Std Err | $IC_{50}$ | Std Err |
| 0401.009.b-03 | 0.0780 | 0.0006 | 0.1120 | 0.0012 | 0.0670 | 0.0075 | 0.1100 | 0.0014 | 0.1100 | 0.0125 |
| 0401.014.b-03 | 0.0140 | 0.0028 | 0.0069 | 0.002 | 0.0078 | 0.00004 | 0.0140 | 0.0024 | 0.0034 | 0.0003 |
| 0401.015.b-03 | 0.0730 | 0.022 | 0.0620 | 0.0050 | 0.0490 | 0.0095 | 0.0680 | 0.0044 | 0.0590 | 0.0073 |

TABLE 3A

Synergistic Inhibition of Proliferation of lung, prostate and colon cancer cells.

| Combination | Cell Line A549 (lung) | | | Cell Line PC-3 (prostate) | | | Cell Line DLD-1 (colon) | | |
|---|---|---|---|---|---|---|---|---|---|
| | IC50 | Std.Dev | Std. Err | IC50 | Std.Dev | StdErr | IC50 | Std.Dev | Std. Err |
| 9 + 14 | 0.0213 | 0.0060 | 0.0035 | 0.0238 | 0.0067 | 0.0033 | 0.0303 | 0.0040 | 0.0020 |
| 9 + 15 | 0.0480 | 0.0061 | 0.0035 | 0.1180 | 0.0838 | 0.0410 | 0.0288 | 0.0118 | 0.0053 |
| 14 + 15 | 0.0293 | 0.0155 | 0.0075 | 0.1143 | 0.0696 | 0.0400 | 0.0195 | 0.0051 | 0.0025 |
| 9 + 14 + 15 | 0.0213 | 0.0081 | 0.0047 | 0.0825 | 0.0126 | 0.0060 | 0.0143 | 0.0095 | 0.0042 |

TABLE 3B

Synergistic Inhibition of Proliferation of breast and prostate cancer cells.

| Combinations of Botanical Extracts | MCF7 IC$_{50}$ | DU145 IC$_{50}$ |
|---|---|---|
| 0401.009.b-03 + 0401.014.b-03 | 0.017 | 0.025 |
| 0401.009.b-03 + 0401.015.b-03 | 0.065 | 0.016 |
| 0401.014.b-03 + 0401.015.b-03 | 0.012 | 0.013 |
| All 3 (9 + 14 + 15) | 0.042 | 0.017 |

All combinations of the three botanical extracts of *Salvia miltiorrhiza* (#14), *Ganoderma lucidum* (#9), and *Scutellaria barbata* (#15) synergistically inhibit proliferation of the human lung cancer cells, breast cancer cells, prostate cancer cells and colon cancer cells as summarized in Table 4.

TABLE 4

Summary of Synergistic Inhibition of Proliferation of lung, breast, prostate and colon carcinoma cells by combinations of botanival extracts.

| Combination Index | A549 lung | MCF7 breast | DU145 prostate | DLD-1 colon |
|---|---|---|---|---|
| 9 + 14 | 0.46 | 0.27 | 0.62 | 0.54 |
| 9 + 15 | 0.63 | 0.74 | 0.27 | 0.30 |
| 14 + 15 | 0.51 | 0.33 | 0.54 | 0.35 |
| 9 + 14 + 15 | 0.55 | 0.43 | 0.28 | 0.23 |

All publications and patent applications cited in this specification are herein incorporated by reference as if each individual publication or patent application are specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of treating colon, lung, breast or prostate cancer in an individual in need thereof comprising administering to said individual a therapeutically effective amount of a composition comprising an ethyl acetate extract of *Ganoderma lucidum* in an amount of about 10 to about 50 percent by weight of the composition, an ethyl acetate extract of *Salvia miltiorrhiza* in an amount of about 10 to about 50 percent by weight of the composition, and an ethyl acetate extract of *Scutellaria barbata* in an amount of about 10 to about 50 percent by weight of the composition, in combination with a therapeutically effective amount of at least one antimetabolite chemotherapeutic agent.

2. The method of claim 1, wherein the composition displays at least one property selected from the group consisting of: anti-inflammatory activity, immunoboosting activity, inducing lymphocytes to release TNF-alpha and inhibiting cell proliferation.

3. The method of claim 2, wherein the anti-inflammatory activity selectively inhibits COX-2 over COX-1.

4. The method of claim 1, further comprising administering to the individual a therapeutically effective amount of one or more additional anticancer treatments selected from the group consisting of radiation therapy, chemotherapy, surgery, immunotherapy, photodynamic therapy, and combinations thereof.

5. The method of claim 1, wherein the cancer is lung cancer selected from the group consisting of small cell lung cancer and non-small cell lung cancer.

6. The method of claim 1, wherein the chemotherapeutic agent is selected from the group consisting of gemcitabine and methotrexate.

7. The method of claim 1, wherein the composition further comprises an organic extract of *Camellia sinensis* (green tea).

8. The method of claim 1, wherein the composition further includes a pharmaceutically acceptable carrier.

9. A method of treating colon, lung, breast or prostate cancer in an individual in need thereof comprising administering to said individual:
   (a) a therapeutically effective amount of a composition consisting of an ethyl acetate extract of *Ganoderma lucidum*, an ethyl acetate extract of *Salvia miltiorrhiza*, and an ethyl acetate extract of *Scutellaria barbata*; and
   (b) a therapeutically effective amount of at least one antimetabolite chemotherapeutic agent.

10. The method of claim 9, wherein the composition displays at least one property selected from the group consisting of: anti-inflammatory activity, immunoboosting activity, inducing lymphocytes to release TNF-alpha and inhibiting cell proliferation.

11. The method of claim 10, wherein the anti-inflammatory activity selectively inhibits COX-2 over COX-1.

12. The method of claim 9, wherein the cancer is lung cancer selected from the group consisting of small cell lung cancer and non-small cell lung cancer.

13. The method of claim 9, wherein the chemotherapeutic agent is selected from the group consisting of gemcitabine and methotrexate.

14. The method of claim 9, wherein the cancer is colon cancer.

* * * * *